United States Patent
Zhang et al.

(10) Patent No.: US 6,464,850 B1
(45) Date of Patent: *Oct. 15, 2002

(54) METHOD FOR PRODUCING HYDROPHILIC MONOMERS AND USES THEREOF

(75) Inventors: Tianhong Zhang, Framingham, MA (US); Noriko Kusukawa, Camden; Mark Garner, Thomaston, both of ME (US)

(73) Assignee: BioWhittaker Molecular Applications, Inc., Rockland, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/363,167

(22) Filed: Jul. 29, 1999

Related U.S. Application Data

(63) Continuation-in-part of application No. 09/127,770, filed on Jul. 31, 1998.

(51) Int. Cl.[7] .................. G02N 27/26; C08F 222/38; B05D 7/22
(52) U.S. Cl. .................. 204/455; 204/469; 526/304; 427/230; 427/384; 427/2.11
(58) Field of Search .................. 204/450, 455, 204/469; 526/304; 427/230, 372.2, 384, 2.11

(56) References Cited

U.S. PATENT DOCUMENTS

| | | | |
|---|---|---|---|
| 2,593,888 A | 4/1952 | Giffin Easton | 564/143 |
| 4,062,831 A | * 12/1977 | Kopecek et al. | 5265/208 |
| 4,101,461 A | 7/1978 | Strop et al. | 521/32 |
| 4,192,784 A | * 3/1980 | Brown et al. | 524/704 |
| 4,568,706 A | * 2/1986 | Noetzel et al. | 521/149 |
| 4,680,201 A | 7/1987 | Hjerten | 427/230 |
| 5,006,210 A | 4/1991 | Yueng et al. | 204/180.1 |
| 5,055,517 A | 10/1991 | Shorr et al. | 524/813 |
| 5,074,982 A | 12/1991 | Novotny et al. | 204/182.8 |
| 5,089,111 A | 2/1992 | Zhu et al. | 204/180.1 |

(List continued on next page.)

FOREIGN PATENT DOCUMENTS

| | | |
|---|---|---|
| JP | 60-262805 | 12/1985 |
| JP | 61-068454 | 4/1986 |
| WO | WO 93/11174 | 6/1993 |
| WO | WO 96/16724 | 6/1996 |
| WO | WO 97/16462 | 5/1997 |

OTHER PUBLICATIONS pp. 93 and 94 from Anthony Andrews (Electrophoresis: Theory, Techniques, and Biochemical and Clinical Applications, snd ed., Clarendon Press, Oxford) 1986 month unknown.*

Caplus abstract of Cervovsky et al. ("Interaction of trypsin with immobilized p–aminobenzamidine derivatives studied by means of affinity electrophoresis", J. Chromatogr. (1980), 194(2), 175–81) month unknown.*

Carrilho et al., "Rapid DNA Sequencing of More Than 1000 Bases per Run by Capillary Electrophoresis Using Replaceable Linear Polyacrylamide Solutions," *Analytical Chem.*, 1996, 68, 3305–3313 Oct.

(List continued on next page.)

*Primary Examiner*—Jill Warden
*Assistant Examiner*—Alex Noguerola
(74) *Attorney, Agent, or Firm*—Woodcock Washburn LLP

(57) ABSTRACT

The invention relates to a method for producing hydrophilic monomers which are particularly useful for electrophoresis and to electrophoresis compositions and coating compositions. The electrophoresis gel compositions and electrophoresis polymer compositions are hydrolytically stable and have high resolution. The method uses the steps of reacting a (meth)acryloyl with an aminoalcohol in the presence of a base in a polar solvent, optionally filtering an aqueous solution of the reaction product, deionizing an aqueous solution of the reaction product, and removing the solvent.

63 Claims, 3 Drawing Sheets

U.S. PATENT DOCUMENTS

| | | | |
|---|---|---|---|
| 5,143,753 A | 9/1992 | Novotny et al. | 427/299 |
| 5,202,007 A | 4/1993 | Kozulic et al. | 204/461 |
| 5,221,477 A | 6/1993 | Melcher et al. | 210/634 |
| 5,306,404 A * | 4/1994 | Notsu et al. | 204/470 |
| 5,319,046 A | 6/1994 | Kozulic et al. | 204/466 |
| 5,464,516 A | 11/1995 | Takeda et al. | 204/182.9 |
| 5,470,916 A | 11/1995 | Righetti | 525/296 |
| 5,534,123 A | 7/1996 | Bashkin et al. | 204/455 |
| 5,552,028 A | 9/1996 | Madabhushi et al. | 204/451 |
| 5,567,292 A | 10/1996 | Makabhushi et al. | 204/451 |
| 5,578,180 A | 11/1996 | Engelhorn et al. | 204/468 |
| 5,605,613 A | 2/1997 | Shieh | 204/451 |
| 5,741,411 A | 4/1998 | Yeung et al. | 204/452 |
| 5,759,369 A | 6/1998 | Menchen et al. | 204/456 |
| 5,863,551 A | 1/1999 | Worely | 424/423 |
| 6,074,542 A * | 6/2000 | Dolnik et al. | 204/454 |
| 6,117,293 A * | 9/2000 | Zhang et al. | 204/455 |

OTHER PUBLICATIONS

Chang et al., "Poly(ethyleneoxide) for high–resolution and high–speed separation of DNA by capillary electrophoresis," *J. Chromatography B*, 1995, 669, 113–123 month unknown.

Chiari et al., "Towards new formulations for polyacrylamide matrices: N–Acryloylaminoethoxyethanol, a novel monomer combining high hydrophilicity with extreme hydrolytic stability," *Electrophoresis*, 1994, 15, 177–186 month uknown.

Deforce et al., "Comparison of slab gel electrophoresis and capillary electrophoresis for the detection of the fluorescently labeled polymerase chain reaction products of short tandem repeat fragments," *J. Chromatography*, 1998, 806(1), 149–155 month unknown.

Dovichi, "DNA sequencing by capillary electrophoresis," *Electrophoresis*, 1997, 18, 2393–2399 month unknown.

Gelfi et al., "Novel acrylamido monomers with higher hydrophilicity and improved hydrolytic stability: III. DNA separations by capillary electrophoresis in poly(N–acryloylaminopropanol)," *Electrophoresis*, 1996, 17, 738–743.

Laemmli, "Cleavage of structural proteins during the assembly of the head of bacteriophage T4," *Nature*, 1970, 277, 680–685 Aug.

Madebhushi, "Separation of 4–color DNA sequencing extension products in noncovently coated capillaries using low viscosity polymer solutions," *Electrophoresis*, 1998, 9, 224–230 month unknown.

Miertus et al., "Molecular modeling of acrylamide derivatives: The case of N–acryloylaminoethoxyethanol versus acrylamide and trisacryl," *Electrophoresis*, 1994, 15, 1104–1111 month unknown.

Chen, "N–(Hydroxyalkyl)acrylamide Copolymers for Corrosion Control," in Polymeric Materials for Corrosion Control, ACS Symposium Series, 1986, 322, 283–390 month unknown.

Chiari, M. et al., "New types of separation matrices for electrophoresis," *Electrophoresis*, 1995, 16, 1815–1829 month unknown.

Saito et al., "Synthesis and Hydrophilicity of Multifunctionally Hydroxylated Poly(acrylamides)," *Macromolecules*, 1996, 29, 313–319 month unknown.

Simò–Alfonso, E. et al., "Novel acrylamido monomers with higher hydrophilicity and improved hydrolytic stability: I. Synthetic route and product characterization," *Electrophoresis*, 1996, 17, 723–731 month unknown.

Simò–Alfonso, E. et al., "Novel acrylamido monomers with higher hydrophilicity and improved hydrolytic stability: II. Properties of N–acryloylaminopropanol," *Electrophoresis*, 1996, 17, 732–737 month unknown.

Baade, "Kinetics of the Dispersions Polymerization of Acrylamide," *Eur. J. Polym. J.*, 1984, 20(5), 505–512 month unknown.

Bocek et al., "Capillary electrohoresis of DNA in agarose solutions at 40° C," *Electrophoresis*, 1991, 12, 1059–1061 month unknown.

Gilges et al., "CZE Separations of Basic Proteins at Low pH in Fused Silica Capillaries with Surfaces Modified by Silane Derivatization and/or Adsorption of Polar Polymers," *J. High Resolution Chromatogr.*, 1992, 15, 452–457 Jul.

Goetzinger et al., "Characterization of high molecular mass linear polyacrylamide powder prepared by emulsion polymerization as a replaceable polymer matrix for DNA sequencing by capillary electrophoresis," *Electrophoresis*, 1998, 19, 242–248.

Heiger et al., "Separation of DNA restriction fragments by high performance capillary electrophoresis with low and zero crosslinked polyacrylamide using continuous and pulsed electric fields," *J. Chromatogr.*, 1990, 516, 33–48 month unknown.

Heller, "Finding a universal low viscosity polymer for DNA separation (II)," *Electrophoresis*, 1998, 19, 3114–3127 month unknown.

Hjertén, "High–Performance Electrophoresis Elimination of Electroendosmosis and Solute Adsorption," *J. Chromatogr.*, 1998, 347, 191–198.

Kim et al., "Separation of DNA sequencing fragments up to 1000 bases by using poly(ethylene oxide)–filled capillary electrophoresis," *J. Chromatogr. A*, 1997, 781, 315–325.

Li et al., "Simple Two–Color Base–Calling Schemes for DNA Sequencing Based on Standard Four–Label Sanger Chemistry," *Appl. Spectrospopy*, 1995, 49(10), 1528–1533.

Tan et al., "Automation and Inteegration of Multiplexed On–Line Sample Preparation with Capillary Electrophoresis for High–Throughput DNA Sequencing," *Anal. Chem.*, 1998, 70(19), 4044–4053 Oct.

* cited by examiner

METHOD FOR PRODUCING HYDROPHILIC MONOMERS AND USES THEREOF

CROSS-REFERENCE TO RELATED APPLICATION

The present application is a continuation-in-part of application Ser. No. 09/127,770, filed on Jul. 31, 1998, incorporated herein by reference.

TECHNICAL FIELD

This invention relates to a method for producing hydrophilic monomers, which are particularly useful for electrophoresis, and to electrophoresis compositions, more particularly, to an electrophoresis gel composition that is hydrolytically stable and has high resolution for biological macromolecule separations. The invention further relates to a polymer composition which effectively suppresses electroendoosmosis, is hydrolytically stable and has high resolution for use in capillary electrophoresis and microchannel-based separations of macromolecules. The invention also relates to the preparation of electrophoresis compositions, electrophoresis gels, and coating compositions. The invention further relates to the use of said compositions, gels and polymer media for high resolution electrophoretic separations of proteins, nucleic acids, and other biological macromolecules.

BACKGROUND ART

The publications and other materials used herein to illuminate the background of the invention and in particular, cases to provide additional details respecting the practice, are incorporated herein by reference.

Electrophoresis gels have been widely used for the separations of biological macromolecules such as proteins, nucleic acids, and the like. There are essentially two types of gels in use: agarose gels and polyacrylamide gels. Polyacrylamide gels, in general, have higher resolving power than agarose gels. Since gel casting is rather tedious and the quality of hand-cast gels is inconsistent, there is a need for precast, "ready to use" gels. Generally, precast gels are manufactured and supplied in buffers of pH between 8 and 9. Under these conditions, precast agarose gels are stable, and have a shelf life of one year at 4° C. However, precast polyacrylamide gels are unstable, and depending on use, have a shelf life of only three months at 4° C. As precast polyacrylamide gels age in alkaline conditions (pH above 7), the electrophoretic mobility of biological macromolecules through these gels decreases and the separation resolution deteriorates. The short shelf life of precast polyacrylamide gels is primarily attributed to the hydrolytic degradation of acrylamide moieties in the gel, while the crosslinking units, usually N,N'-methylene bisacrylamide, are relatively stable. Due to the short shelf life of precast polyacrylamide gels, it is difficult for a manufacturer to mass-produce and to store large quantities of gels, and it is inevitable that some customers have to throw away some unused but "expired" gels. Therefore, it is highly desirable to have a gel that has a similar resolution to polyacrylamide gel, but a longer shelf life. Since the manufacturing and application of precast polyacrylamide gels are well established, it is even more desirable to have a stable, high resolution gel system that can be manufactured and used in the same manner as polyacrylamide gels.

Recognizing the fact that the short shelf life of precast polyacrylamide gels is due to the hydrolytic degradation of acrylamide moieties in alkaline condition, Takeda et al. (U.S. Pat. No. 5,464,516), Engelhorn et al. (U.S. Pat. No. 5,578,180) and Bjellqvist et al. (WO 96/16724) developed neutral buffer systems to replace the conventionally used Tris-HCl buffer (pH=8.8) in sodium dodecyl sulfate (SDS) polyacrylamide gels to reportedly improve the shelf life of precast polyacrylamide gels. However, the gel running buffer has to be changed to be compatible with gel buffer, and the protein separation patterns that are obtained from these systems are different from traditional SDS polyacrylamide electrophoresis based on the Laemmli system (Laemmli, *Nature* 277:680–685 (1970)).

Several vinyl-based monomers were proposed to replace acrylamide in the standard polyacrylamide gel system in order to improve gel stability. Shorr and Jain (U.S. Pat.No. 5,055,517) disclosed the use of N-mono- or di-substituted acrylamide monomers, such as N,N'-dimethylacrylamide (DMA), in electrophoresis gels. Although DMA is more stable than acrylamide, DMA is very hydrophobic and is useful in only a limited number of electrophoretic applications, such as for certain types of nucleic acid analyses.

Kozulic and Mosbach (U.S. Pat. No. 5,319,046) disclosed the use of N-acryloyl-tris-(hydroxymethyl)aminomethane (NAT), and Kozulic (U.S. Pat. No. 5,202,007) disclosed the use of sugar-based acrylamide derivatives in electrophoresis gels. Because of the presence of several hydroxyl groups in the monomers, these monomers are extremely hydrophilic. However, Chiari et al (*Electrophoresis* 15:177–186 (1994)) reported that NAT is less stable than acrylamide. On the basis of molecular modeling, Miertus et al (*Electrophoresis* 15:1104–1111 (1994)) concluded that, when there are two atoms between the amide linkage and the hydroxyl group (as is the case for NAT, sugar-based acrylamide derivatives, and N-(2-hydroxyethyl)acrylamide), the hydroxyl group facilitates the hydrolysis of amide linkages.

In a series of articles and a U.S. patent, Righetti et al. (U.S. Pat. No. 5,470,916; *Electrophoresis* 15:177–186 (1994); *Electrophoresis* 16:1815–1829 (1995)) disclosed the use of N-mono- and di-substituted hydroxyethoxyethyl-(meth)acrylamides and their analogs in electrophoresis gels. The formula of the monomers disclosed by Righetti et al. in these

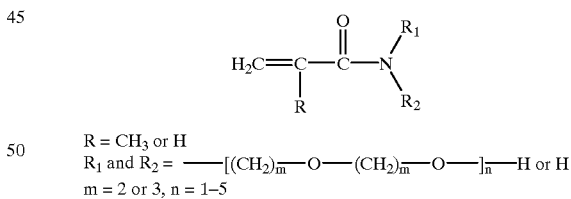

R = CH$_3$ or H
R$_1$ and R$_2$ = ———[(CH$_2$)$_{\overline{m}}$—O——(CH$_2$)$_{\overline{m}}$—O——]$_{\overline{n}}$—H or H
m = 2 or 3, n = 1–5

N-(Hydroxyethoxyethyl)acrylamide (HEEAA) was identified as the preferred monomer, because of its extreme hydrophilicity and resistance to alkaline hydrolysis.

However, Righetti et al. (WO 97/16462; *Electrophoresis* 17:723–731 (1996); *Electrophoresis* 17:732–737 (1996); *Electrophoresis* 17:738–743 (1996)) subsequently reported that the HEEAA monomer had a peculiar tendency to auto-polymerize during storage as a 50% aqueous solution at 4° C., even in the presence of free radical inhibitor. In view of this auto-polymerization tendency of HEEAA, Righetti et al. disclosed in these references the use of N-mono- and di-substituted hydroxyalkyl-(meth)acrylamides as an alternative in electrophoresis gels. The formula of the monomers disclosed by Righetti et al. in these references is:

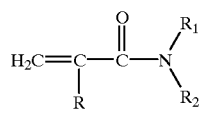

R = CH$_3$ or H
R$_1$ and R$_2$ = ——[(CH$_2$)$_{\overline{m}}$—O——]$_{\overline{n}}$—H or H
m> = 3, n = 1–5

N-(Hydroxypropyl)acrylamide (HPAA) was claimed by Righetti et al. to be extremely hydrophilic and resistant to alkaline hydrolysis. However, to applicants' knowledge there have been no further reports on HPAA-based gels by Righetti's group or other groups, and there have been no HPAA-based commercial products.

For capillary electrophoresis (CE) of biological molecules, linear non-crosslinked polymers are commonly used rather than crosslinked gels due to easy replacement of media between runs. Many water-soluble, non-ionic polymers were shown to have utility as sieving media for CE. These include polyacrylamide (*J Chromatogr*, 516:33–48 (1990)), substituted celluloses (U.S. Pat. No. 5,534,123), polyethylene oxide (*J Chromatogr* 781:315–25 (1997)), and polyacrylamide derivatives (U.S. Pat. Nos. 5,552,028 and 5,567,292) for capillary-based DNA sequencing. For CE of double-stranded DNA fragments, agarose (*Electrophoresis* 12:1059–1061 (1991)), polymers made from N-substituted acrylamide monomers (*Electrophoresis* 15:177–186 (1994); *Electrophoresis* 17:723–731 (1996); U.S. Pat. No. 5,470,916), polyvinyl alcohol, and polyvinylpyrrolidone (U.S. Pat. No. 5,089,111) are known. These suggest that any hydrophilic, non-charged polymer will have some utility in electrophoretic separation of biological molecules in capillaries (*Electrophoresis* 19:3114–3127 (1998)).

A problem in capillary electrophoresis (CE) is electroendoosmosis (EEO) which must be lo suppressed in order to obtain good resolution of analytes. Typically, the capillaries used in CE are fused silica glass. The silanol groups on the inner surface of capillaries will become negatively charged under the alkaline pH of separation buffers, and because these are fixed charges, when a high voltage is applied (>100 V/cm) the mobile solution in the capillary is pulled toward the cathode. This phenomenon, termed EEO, retards the migration of negatively charged analytes such as DNA and proteins, and obscures the ability of the system to accurately separate them by size. Therefore, it is necessary to neutralize or shield the charges on the capillary wall to suppress EEO. There are two methods to solve this problem: (1) to perform chemical modification of the capillary wall, and (2) to use polymers that adsorb to the capillary wall.

There are several known methods that apply chemical modification of the capillary glass surface to suppress EEO.

Hjertén (U.S. Pat. No. 4,680,201; *J Chromatogr* 347:191–198 (1998)) described a method in which he reacted the silanol groups on the capillary wall with a bifunctional silane reagent, such as methacryloylpropyl trimethoxysilane, to introduce vinyl groups on the capillary wall. A polyacrylamide layer is attached to it by polymerization of acrylamide to coat the wall. While this method is widely used, the coating degrades under the high temperature alkaline conditions used in electrophoresis due to hydrolysis of the Si-O-Si bonds. Also, the amide groups on polyacrylamide will undergo hydrolysis and result in charged moieties. Either of these will lead to a buildup of charge on the capillary wall, and will be observed as an increase in EEO and decrease in resolution.

Novotny et al. (U.S. Pat. Nos. 5,074,982, 5,143,753) described a partial solution to the problem by use of Grignard chemistry to introduce more stable anchoring sites for the vinyl groups on the wall by use of Si-C bonds, but this still did not address the instability of the amide groups on the polyacrylamide coating.

To overcome the hydrolysis of acrylamide, Righetti et al described the use of stable substituted acrylamide monomers as coating composition for the inner walls of capillaries in combination with the Grignard chemistry (U.S. Pat. No. 5,470,916 and WO97/16462). In this disclosure, Righetti reports that N-(2-hydroxyethyl)acrylamide (HEAA) is not useful due to instability (*Electrophoresis* 15:1104–1111 (1994)).

An alternative approach to the chemical treatment of capillaries is to use polymers which directly interact with or adsorb to the capillary wall, resulting in a transient "coating" or zone of high viscosity which suppresses EEO. This approach is less tedious and time-consuming compared to the preparation of chemically coated capillaries, and operationally less expensive because the capillaries do not need to be replaced as often as the chemically treated capillaries. The polymer solution could have a dual function, (1) as coating of capillary surfaces and (2) as media for effective molecular separation.

It was demonstrated by Gilges and coworkers that non-ionic polyvinylalcohol was useful for protein electrophoresis in bare fused silica capillaries (*J High Resolution Chromatography* 15:452–457 (1992)). Yeung and co-workers reported that even pre-washing a capillary with polyvinylpyrrolidone (PVP) gives enough adsorption of PVP to the capillary wall that it can be re-filled with another polymer solution useful for DNA sequencing (*Anal Chem* 70:4044–4053 (1998)). These two reports suggest that most hydrophilic non-ionic polymers can adsorb to bare silica surfaces and suppress EEO. In theory, such capillaries may be reused multiple times, provided that the coating can be washed away by refilling of polymer, or stripped off by acid treatment between uses, and thereby, fresh coating is regenerated for each use. In a practical sense, however, it is not easy to completely remove the coating between uses, and build up of hydrolytically unstable polymers on the capillary wall will become a problem as it will be the cause of increase in EEO.

Madabhushi et al (U.S. Pat. Nos. 5,552,028 and 5,567,292) reported that poly(N,N-dimethylacrylamide) is capable of suppressing EEO when injected into a bare fused-silica capillary, and that it can provide high performance in molecular separation for repeated use (U.S. Pat. Nos. 5,552,028 and 5,567,292). Poly(N,N-dimethylacrylamide) is now commercially available from PE Biosystems as the "POP" matrix for use in DNA sequencing and fragment analyses in CE (*Electrophoresis*, 1998. 19, 224–230). The disadvantage of POP, however, is that it lacks resolution in the high molecular weight region and gives shorter read lengths in DNA sequencing compared to the classical linear polyacrylamide. Madabhushi et al also discloses N-substituted polyacrylamides, in which one possible substituent is hydroxyl-substituted $C_1$ to $C_3$ alkyl, as useful for this application, but are not specific as to which compounds are particularly useful. Furthermore, Madabhushi et al restricts the molecular weight of such polymers to be between 5,000 to 1,000,000 Daltons. Although Madabhushi et al relies heavily on the self-coating aspect of the polymer, they do not teach how to improve resolution.

Although N-(2-hydroxyethyl)acrylamide (HEAA) is an analog of the N-(hydroxyalkyl) acrylamides disclosed by Righetti (WO 97/16462), it has never been specifically reported as a monomer for electrophoresis gels. For example, Righetti specifically excludes HEAA in his patent applications and references. This is partially because HEAA was not commercially available, but more importantly, HEAA was believed to be unstable to hydrolysis, like N-acryloyl-tris-(hydroxymethyl)aminomethane (NAT) (*Electrophoresis* 15:1104–1111 (1994)).

Several preparation methods for HEAA have been reported in the literature. Saito et al (*Macromolecules* 29:313–319 (1996)) described a two-phase method for the preparation of HEAA. The organic phase contains acryloyl chloride and ethyl acetate solvent, and the aqueous phase contains sodium hydroxide and ethanolamine. The product is recovered from the organic phase, and further purified by silica gel chromatography. There are two inherent disadvantages with this method, however. First, HEAA is readily soluble in water, and ethyl acetate extraction is not efficient. Second, it is impractical to produce large quantities of HEAA by silica gel chromatography.

Chen (*ACS Symposium Series* 322:283–290 (1986)) disclosed a one-phase method in which acryloyl chloride was reacted with two equivalents of ethanolamine in acetonitrile. Although high-yield HEAA can be obtained in acetonitrile solution, no purification method was provided, other than removing acetonitrile by distillation. Removal of acetonitrile in this manner results in some polymerization of the HEAA monomer during purification.

Righetti et al (WO 97/16462; *Electrophoresis* 17:723–731 (1996)) disclosed another one-phase method for the preparation of N-(hydroxyalkyl)acrylamides. They reported that ethanol is the best solvent for this reaction. Since ethanol is reactive towards acryloyl chloride, the reaction has to be conducted between −30° C. and −70° C. Silica gel was also used for further purification.

Murashige and Fujimoto (JP 61-068454 and JP 61-000053) disclosed a method in which N-(hydroxyethyl) acrylamide was prepared by treating ethanolamine with $C_{1-22}$ alkyl acrylate or acrylic acid. The monomer was directly converted to its polymer, and no monomer purification method was disclosed.

Jones (U.S. Pat. No. 2,593,888) describes the preparation of hydroxyalkyl(meth)acrylamide monomers in a reported high state of purity, as well as the polymerization of these monomers to produce water-soluble polymers. One monomer, HEAA, is prepared by reacting an excess of ethanolamine with acryloyl chloride in acetonitrile at a reduced temperature, followed by filtration and solvent removal.

Thus, there is a need to develop additional hydrophilic monomers for preparing electrophoresis compositions, and particularly electrophoresis gels having the combined properties of hydrolytic stability and high resolution. This need in the art is satisfied by the present invention, as described in further detail below.

There is also a need to develop additional linear polymers, particularly for capillary electrophoresis and microchannel-based separations, having the combined properties of suppressing electroendoosmosis, hydrolytic stability and high resolution. This need in the art is satisfied by the present invention, as described in further detail below.

There further is a need to develop a method for producing high purity N-(hydroxy-ethyl)acrylamide (BEAA) and similar hydrophilic monomers simply and on a large scale. This need is satisfied by the present invention, as described in further detail below.

DISCLOSURE OF THE INVENTION

It is an object of this invention to provide a method for the preparation of high-purity hydrophilic acrylamide or methacrylamide derivatives containing hydroxy groups simply and on a large scale.

It is also an object of this invention to provide compositions useful for electrophoresis, including pre-cast gels and monomer compositions for coating capillaries or for preparing electrophoresis gels or polymers, for the separation of biological macromolecules, such as proteins, nucleic acids and the like.

It is a further object of this invention to provide a gel composition for electrophoretic separations, which has combined high resolution and hydrolytic stability.

It is also an object of this invention to provide a linear polymer for capillary electrophoresis that effectively suppresses electroendoosmotic flow and at the same time gives high performance in electrophoretic separation of analytes in capillaries.

As used herein, the terms (meth)acryloyl chloride, (meth) acrylic acid and (meth)acrylamide are intended to refer to acryloyl or methacryloyl chloride, acrylic or methacrylic acid and acrylamide or methacrylamide, respectively.

According to one aspect of the present invention, hydrophilic monomers are produced by reacting (meth)acryloyl chloride with an aminoalcohol in a polar solvent, which favors amidation in the presence of a base. The reaction mixture is subjected to deionization, solvent removal and optionally, filtration. In one embodiment of the invention, water is added to the reaction mixture, the resulting aqueous solution is deionized, and the solvent is removed from the deionized aqueous solution to produce an aqueous solution of the hydrophilic acrylamide or methacrylamide derivatives containing hydroxy groups free of solvent. In a second embodiment of the invention, water is added to the reaction mixture, the solvent is removed from the resulting aqueous solution, and the resulting aqueous solution free of solvent is deionized to produce an aqueous solution of the hydrophilic acrylamide or methacrylamide derivatives containing hydroxy groups. In a third embodiment, the reaction mixture is first filtered to remove the salt byproduct prior to the addition of water for deionization or for the solvent removal step.

According to a second aspect of the invention, compositions useful for electrophoretic applications are provided. In one embodiment, these compositions may be used for coating capillary tubes used for capillary electrophoresis or to prepare a linear polymer as the sieving medium for capillary electrophoresis. In this embodiment, the composition comprises an aqueous solution of either the hydrophilic monomer (for coating) or the linear polymer (for use as a sieving medium). The linear polymer composition for use in capillary electrophoresis and microchannel-based separations of macromolecules effectively suppresses electroendoosmosis, is hydrolytically stable and has high resolution. In a second embodiment, the composition may also be used to prepare formulated solutions, which can be used to prepare precast gels or to prepare gels prior to use. Such gels are useful for DNA sequencing or other macromolecule separations. In this embodiment, the composition comprises a hydrophilic N-(hydroxyalkyl) (meth)acrylamide or N,N-di (hydroxyalkyl)(meth)acrylamide monomer, an optional comonomer, a bifunctional crosslinker, such as N,N'-methylene bisacrylamide (BIS), a buffer and an optional denaturant. An initiator is added to effect the formation of the gel.

According to a third aspect of the invention, a stable, high-resolution electrophoresis gel is prepared by the free radical copolymerization of a hydrophilic monomer as described herein, preferably N-(2-hydroxyethyl)acrylamide (HEAA), an optional comonomer, and a bifunctional crosslinker, such as N,N'-methylene bisacrylamide (BIS), in a buffer solution in a plastic or glass gel mold.

DETAILED DESCRIPTION OF THE INVENTION

Figure 1:
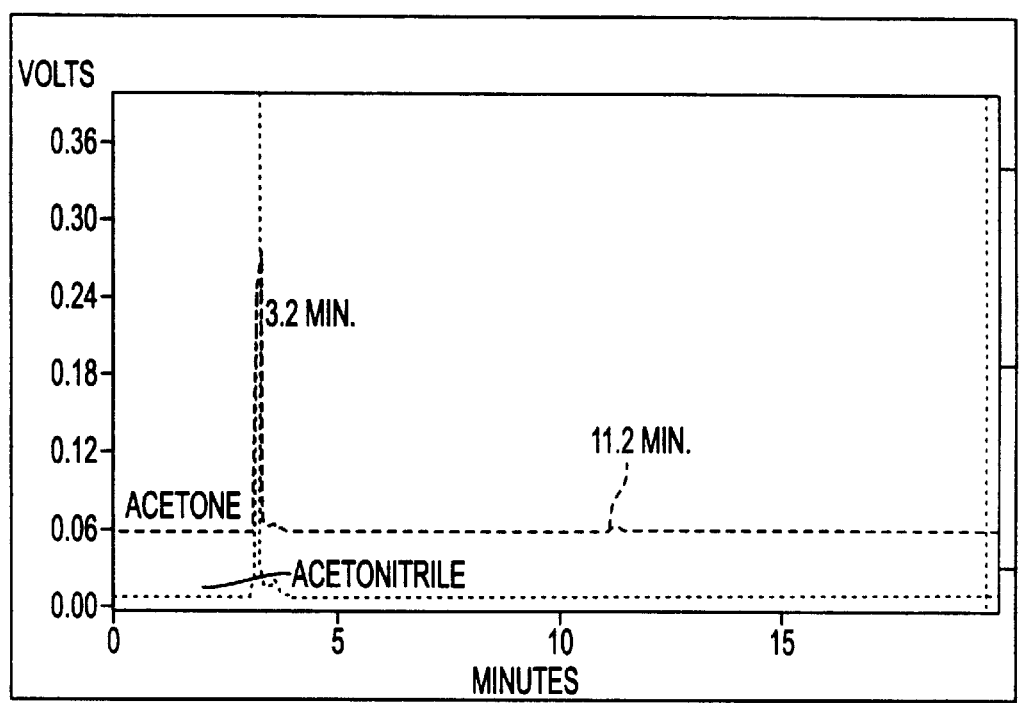
FIG. 1 shows a high performance liquid chromatography (BPLC) chromatogram of HEAA reaction products prepared in acetone (top graph line) or acetonitrile (bottom graph line). HPLC analysis was conducted with a Rainin Dynamax Model SD-200 solvent delivery system equipped with a UV detector. The following running condition was used: Column, Reverse Phase Hypersil ODS 5 mm from Aldrich; Mobile Phase, 10% acetonitrile and 90% water mixture; Flow Rate, 1.0 mL/minute; Detection, 254 nm.

The large-scale preparation of high purity hydrophilic monomers for use in electrophoresis, especially HEAA, has been a challenge for two reasons. First, HEAA is prepared by reacting acryloyl chloride with a bifunctional compound, ethanolamine. While amidation of the amine group on ethanolamine is the desired reaction, esterification of the hydroxyl group on ethanolamine is also possible. Therefore, in addition to the desired product, HEAA, there are two possible byproducts, aminoethyl-acrylate and acrylamido-ethyl-acrylate. The chemical structures of these compounds are shown below:

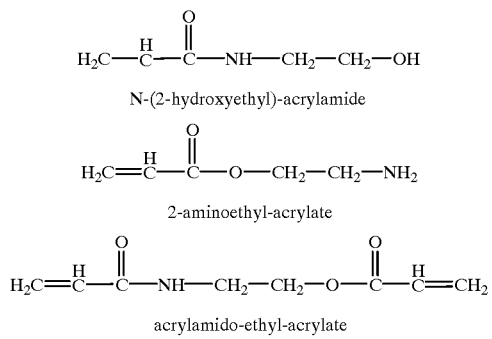

N-(2-hydroxyethyl)-acrylamide 2-aminoethyl-acrylate acrylamido-ethyl-acrylate

While aminoethyl-acrylate can be removed by ion exchange, the separation of the hybrid crosslinker, acrylamido-ethyl-acrylate, from the desired monomer, HEAA, is difficult. In order to minimize or eliminate esterification, it is preferred to conduct the reaction at low temperature. Secondly, HEAA is a liquid with a high boiling point, and neither crystallization nor vacuum distillation is suitable as a purification method. For small-quantity preparation, silica gel chromatography has to be used. In addition, Applicants have found that HEAA has a high tendency to self-polymerize.

According to one aspect of the present invention, a method is provided for preparing hydrophilic monomers having high purity in a simple manner and on a large scale. The method to prepare high purity hydrophilic monomers has the following advantages over prior art methods: (1) the reaction can be conducted at temperatures about or above 0° C. without esterification; (2) self-polymerization of hydrophilic monomers, especially those which underwent self-polymerization by prior art methods, is eliminated by keeping the monomer in solution throughout the process; (3) the hydrophilic monomer is purified by deionization, preferably by ion-exchange rather than silica gel columns, as in the prior art. The method of the present invention for preparing the hydrophilic monomers involves three or four steps, as described below. The steps can be conducted in several combinations, as described below.

One step involves the reaction of a (meth)acryloyl chloride having the following formula

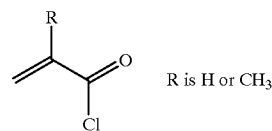

R is H or $CH_3$ with an equivalent amount of an aminoalcohol having the following formula $NH(R_1)(R_2OH)$ wherein $R_1$ is H, $C_1$–$C_6$ alkyl, $(C_1$–$C_3$ alkyl-X—$)_n$—H, $C_1$–$C_3$ alkyl-C(O)—$OR_3$ or $(C_{1C3}$ alkyl-C(O)—NH—$R_4$, $R_2$ is $C_2$–$C_6$ alkyl, $(C_1$–$C_3$ alkyl-X—$)_n$—H, $C_1$–$C_3$ alkyl-C(O)—$OR_3$ or $(C_1$–$C_3$ alkyl-C(O)—NH—$R_4$, $R_3$ is $C_1$–$C_3$, $R_4$ is H or $C_1$–$C_3$, X is O or S, n is 1–5, each alkyl is a linear or branched chain alkyl and is unsubstituted or substituted with halogen, hydroxy or other non-ionizable group in the presence of a base in a polar solvent at a temperature below 20° C., preferably below 5° C., and most preferably below 0°C. The solvent is selected such that (1) it favors amidation and disfavors esterification. In addition, in a preferred embodiment, the solvent is further selected such that (2) it is anhydrous to avoid hydrolysis of the (meth) acryloyl chloride. In a more preferred embodiment, the solvent is further selected such that (3) it is aprotic, (4) it has a lower boiling point than water and (5) the ammonium chloride salt has a low solubility in the solvent. The selection of solvent other than for factor (1) can be chosen on the basis of the further steps described below. Any organic solvent, which meets these criteria, can be used. Suitable solvents include, but are not limited to, acetonitrile and ethanol. The base may be the aminoalcohol or a tertiary amine. Suitable tertiary amines include, but are not limited to, triethylamine and pyridine. A preferred base is one which forms insoluble HCl salts in the organic solvent. The temperature at which the reaction is conducted is dependent on the solvent used, and is selected to avoid esterification and polymerization of the monomer as it is being prepared. For example, if the solvent is acetonitrile, a temperature below 5° C. is preferred, whereas if the solvent is ethanol, a temperature below −20° C. is preferred. It is preferred to use acetonitrile as the polar solvent. The reaction is preferably conducted at a 0.5–3.0 M concentration of reactants, more preferably at a 1.0–2.0 M concentration of reactants, and most preferably at a 2.0 M concentration of reactants. The reaction is conducted to give a final product concentration preferably in the 10%–40% range, more preferably in the 15%–35% range, and most preferably in the 20%–30% range. The reaction produces a hydrophilic monomer having the following formula

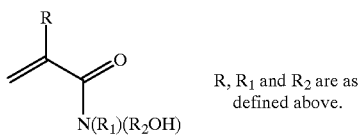

R, R$_1$ and R$_2$ are as defined above.

A second step involves the filtration of the reaction mixture to remove a majority of the ammonium chloride salt and the conversion of the filtrate to an aqueous solution by the addition of water. If filtration is used to remove a majority of the salts, it is preferred to use a solvent in which the salts have a low solubility.

A third step involves the removal of solvent from an aqueous solution. The aqueous solution is prepared prior to solvent removal either directly, by the addition of water, or as the result of a prior step, such as the addition of water either (a) to a filtrate as noted above for the second step, or (b) to the reaction mixture prior to deionization. Solvent is removed from the aqueous solution by conventional techniques, such as vacuum distillation (evaporation) or phase extraction. If the solvent is removed by vacuum distillation, it is necessary to use a solvent which has a boiling point below that of water. If the solvent is removed by phase extraction, the solvent can have a boiling point higher than water. The solvent is removed while keeping the solution temperature below 25° C., which results in a final aqueous solution containing 10–50% of hydrophilic monomer.

A fourth step involves the purification of the hydrophilic monomer by ion exchange, i.e., a deionization step, from an aqueous solution. The aqueous solution is prepared prior to deionization either directly, by the addition of water to the reaction mixture to be deionized, or as the result of a prior step, such as either (a) addition of water to the filtrate following filtration or (b) addition of water to the reaction mixture prior to solvent removal. Any method can be used for removing all of the ionic moieties (primarily aminoalcohol, hydrochloride (HCl) and (meth)acrylic acid) from the aqueous solution. In one embodiment, the deionization is performed by passing the aqueous solution through a mixed-bed ion-exchange column. Alternatively, deionization is performed in a batch process by adding a mixed-bed ion exchange to the aqueous solution and then filtering the solution to remove the ion-exchanger. Deionization can also be performed using a cationic exchanger and an anionic exchanger in series.

The deionized, solvent-free, aqueous solution is the final product which can be used either directly as described herein or concentrated further for storage. The hydrophilic monomer produced in accordance with this process has high purity. Specifically, the hydrophilic monomer solution does not contain any detectable amount of (1) esterification products, (2) oligomers or (3) salts. Thus, the hydrophilic monomer solution produced in accordance with this process can be used directly.

Several combinations of the above steps can be used in accordance with the present invention to produce the hydrophilic monomers. These combinations are outlined as follows:

Embodiment A: reaction→filtration→solvent removal→deionization;

Embodiment B: reaction→filtration→deionization→solvent removal;

Embodiment C: reaction→solvent removal→deionization; and

Embodiment D: reaction→deionization→solvent removal.

Water is added before deionization or solvent removal for two reasons. One is to prevent the self-polymerization of resultant hydrophilic monomer at a concentrated state, and the other is to facilitate purification by ion exchange. When using solvent evaporation as the means to remove the solvent, it is currently preferred to use either embodiment B or D above for the preparation of hydrophilic monomers according to the present invention. When using phase extraction as the means to remove the solvent, any embodiment can be used. It is preferred to deionize the aqueous solution prior to solvent removal, to prevent a minor amount of self-polymerization, which may occur if the solvent is removed prior to deionization. In accordance with the above description, the preparation of hydrophilic monomers in high purity and high yield, in a simple manner on a large scale in accordance with the preferred embodiments of the present invention, is performed by (i) conducting the reaction to avoid esterification, (ii) deionizing the resulting reaction mixture before solvent removal, and (iii) removing the organic solvent. The product has the following properties: (1) it is free of the hybrid crosslinker, the byproduct formed by reactions of both the amino and hydroxy groups on the aminoalcohols with (meth)acryloyl chloride, according to HPLC analysis; (2) it contains 10–50% hydrophilic monomer; (3) it has a pH of 5–9 at 25° C.; (4) it has a conductivity below 100 $\mu$S/cm at 25° C. and (5) it has a viscosity of no more than 10 cPs at 25° C.

The hydrophilic monomers of the present invention, selected from the group consisting of N-(hydroxyethyl)acrylamide or N-(hydroxyethyl)methacrylamide (hereinafter N-(hydroxy-ethyl)(meth)acrylamides) or N,N-di(hydroxyethyl)acrylamides or N,N-di(hydroxyethyl)methacrylamides (hereinafter N,N-di(hydroxyethyl)(meth)acrylamides) and mixtures thereof, preferably HEAA, can be used in electrophoresis applications well known in the prior art, including separation of macromolecules such as proteins and DNA, in gel electrophoresis or capillary electrophoresis, in sequencing DNA and coating capillary electrophoresis tubes. In these applications, the hydrophilic monomer is used in place of all or part of the acrylamide. Thus, the present invention also provides gels and electrophoresis compositions based on these specified monomers, preferably HEAA. In the discussion, which follows, specific reference will be made to HEAA-based gels for illustration purposes only. It is to be understood that any of the specified hydrophilic monomers or mixtures thereof can be used for preparing the gels and electrophoresis compositions described herein.

The HEAA-based electrophoresis gels are prepared in a similar way to polyacrylamide gels, with the exception that HEAA monomer is substituted for all or part of the acrylamide monomer. Therefore, typical HEAA-based gels are formed in electrophoresis buffers by the free radical copolymerization of HEAA and optional comonomer with crosslinker, N,N'-methylene bisacrylamide (BIS) using ammonium persulfate (APS) and N,N,N',N'-tetramethylethylenediamine (TEMED) as initiator. In addition, the HEAA-based gels may also contain a denaturant such as, but not limited to, urea or N-methylpyrrolidinone. The usable gel concentration (%T) (%T= (($W_{monomer}$+$W_{crosslinker}$)/$W_{gel}$)×100) is from 3% to 30%. Since HEAA has a higher formula weight (F.W.=115) than acrylamide (F.W.=71), the crosslinker level on a weight basis (%C) ($\%C = (W_{crosslinker}/(W_{monomer}+W_{crosslinker})) \times 100$) in HEAA-based gel needs to be reduced in order to keep the crosslinking density of the gel at about the same level. The Examples herein demonstrate the applications of HEAA-based gels for the electrophoretic separations of proteins, double-stranded DNA fragments, and automated DNA sequencing. These examples show that HEAA-based gels rival the resolution of polyacrylamide gels, and often have a longer shelf life than polyacrylamide gels.

Comonomers which can be used in combination with HEAA are water-soluble monomers including, but not limited to, acrylamide, methacrylamide, N,N-dimethylacrylamide (DMA), isopropylacrylamide, N-methylolacrylamide, N-vinylpyrolidone, N-vinylfomiamide, N-vinyl acetamide, other mono- and di-substituted hydroxyalkyl (meth)acrylamides of this invention, hydroxyethyl(meth)acrylate, polyethylene glycol mono(meth)acrylates, olefinic agarose and the like. The selection of comonomer is dependent on the specific electrophoretic application. For example, if protein separations are performed, it has been found that DMA is not useful as a comonomer. As with polyacrylamide gels, crosslinkers having polymerizable olefinic unsaturation may be used with the HEAA monomer in place of BIS to prepare electrophoresis gels. Crosslinkers are used in an amount of about 0.01%C to about 2.0%C. Such suitable crosslinkers include, but are not limited to, piperazine diacrylamide (PDA), bisacrylamide-methyl-ether (BAME), N,N'-diallyl-tartardiamide (DATD), ethylene diacrylate, ethylene dimethacrylate, N,N'(1,2-dihydroxyethylene)bisacrylamide, N,N',N"-triallycitric triamide, poly(ethylene) glycol diacrylate, N,N'-bisacryloyl cystamine and olefinic agarose and the like.

In addition to APS/TEMED, other free radical polymerization initiators such as thermal/chemical initiators and photoinitiators can be used. Thermal/chemical initiators include, but are not limited to, benzoyl peroxide, t-butylhydroperoxide, hydrogen peroxide-$Fe^{2+}$-ascorbic acid, persulfate salts in conjunction with dimethylethylenediamine (DEMED), or β-dimethyl-aminopropionitrile, ammonium persulfate-metabisulfite, persulfate-TEMED-hydrosulfite, 2-(carbamoylazo)isobutyronitrile, 2,2'-azobis (N,N'-dimethyleneisobutyramidine)dihydrochloride, and 2,2'-azobis(2-amidino-propane)dihydrochloride.

Photoinitiators of aqueous soluble or dispersible compounds include, but are not limited to, riboflavin; mono- and di-carbonyl compounds, such as benzoylcyclohexanol, acetophenones (di- or tri-) substituted at the 2 position, 2,2 dimethoxy-2-phenylacetophenone, 2,2-diethoxyacetophenone, 2-hydroxy-2-methyl-1-propiophenone, 2 methoxy-2-phenylacetophe-none, Michler's ketone [4,4'-bis(dimethylamino)-benzophenone], 4-carboxybenzophenone, benzophenone, diamino benzophenone, 9,10-phenanthrenequinone-3-sulfonate potassium salt, 1,2-naphthol-quinone-2-sulfonate potassium salt, 1,4-naphthoquinone-2-sulfonate potassium salt, 4-trichloromethyl-4-methyl-2,5-cyclohexadienone, benzoin ethers such as benzoin methyl ether and other benzoins, fluoroenones, and other aromatic water-soluble or dispersible mono- and di-carbonyl compounds; dyes such as methylene blue, new methylene blue, xanthine dyes, acridine dyes, thiazine dyes, phenazine dyes, camphorquinone dyes. Photoinitiators can be used with hydrogen donors including N,N-dimethylaminobenzoic acid, N,N'-dimethylaminoethanol, N-methyl diethanol amine, sodium p-toluene sulfate, and triethanolamine.

In addition to precast gels, preformulated compositions for use in electrophoresis are also provided by the present invention. The preformulated solutions comprise the ingredients listed above with respect to the HEAA-based gels in a suitable electrophoresis buffer, such as TBE, except the free radical initiator is not included. Gels are made from preformulated compositions by the addition of a free radical initiator.

Compositions for use in capillary electrophoresis include a coating composition and a sieving composition. The coating composition for capillary electrophoresis comprises an aqueous solution of HEAA monomer or linear polymer of HEAA. The sieving composition comprises an aqueous solution of HEAA linear polymer, at a concentration of 0.001% wt/vol to 30% wt/vol. As with electrophoretic gels, the linear polymer may be an HEAA homopolymer or a copolymer of HEAA and one or more comonomers. The molecular weight of the polymer is in the range of $1 \times 10^5$ to $20 \times 10^6$, preferably in the range of $1 \times 10^6$ to $10 \times 10^6$. The method to coat electrophoresis tubes for capillary electrophoresis with a vinyl monomer solution is described in U.S. Pat. Nos. 4,680,201, 5,221,447 and 5,605,613. Coating of capillaries by linear polymer is described by Gilges et al. (*J. High Resolution Chrom.* 15:452–457 (1992), Tan and Yeung (*Anal. Chem.* 70:4044–4053 (1998) and U.S. Pat. No. 5,552,028. Separation and sequencing of DNA by capillary electrophoresis have been described by Dovichi (*Electrophoresis* 18:2393–2399 (1997)), Cheng et al. (*J. Chromatography B.* 669:113–123 (1995)), Carrilho et al. (*Analytical Chemistry* 68:3305–3313 (1996)), and Madabhushi (*Electrophoresis* 9:224–230 (1998)).

Electrophoretic methods using the specified hydrophilic monomers alone or in combination with comonomers, preferably acrylamide, are performed using conventional techniques. It has been found that gels and linear polymers prepared in accordance with the present invention have as good of resolution as seen for acrylamide gels or linear polymers of acrylamide.

EXAMPLES

The present invention is described by reference to the following Examples, which are offered by way of illustration and are not intended to limit the invention in any manner. Standard techniques well known in the art or the techniques specifically described below were utilized. All raw materials were purchased from Aldrich Chemical Company, Milwaukee, Wis., and used as received, unless otherwise specified. Acryloyl chloride and methacryloyl chloride were used directly or were distilled before use. The mixed-bed ion-exchange resin Amberlite™ MB-150 was washed with appropriate solvent before use, as recommended by the manufacturer.

Example 1
Preparation of HEAA by Prior Art Method

In this example, HEAA was prepared according to the procedure reported by Chen (*ACS Symposium Series* 322:283–290 (1986)).

To a one liter, four-neck, round bottom flask equipped with a mechanical stirrer, a thermometer, a 400 mL dropping funnel, and nitrogen inlet/outlet, 122 g of ethanolamine (2 moles) and 250 mL of acetonitrile were added. The mixture was cooled down to −15° C. with an ice/water/salt bath. To this cold solution, 94.3 g of acryloyl chloride (1 mole) in 250 mL of acetonitrile was added through the dropping funnel. The addition rate was controlled so that the reaction temperature was kept about −15° C. After the reaction, the mixture was filtered to remove ethanolamine.HCl salt. To the filtrate, 300 mg of 4-methoxyphenol was added, and acetonitrile was removed by vacuum distillation. The solution temperature was kept below 25° C. to prevent free radical polymerization. The complete removal of acetonitrile resulted in either a viscous liquid or a solid mass. The viscous liquid is soluble in water, but the aqueous solution had a very high viscosity. The solid mass could not be dissolved in water. It is believed that polymerization by Michael addition reaction occurred during acetonitrile removal. The polymerization reaction is shown below:

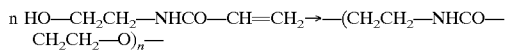

At a low level of polymerization, water-soluble oligomers were formed. At a high level of polymerization, water-insoluble polymers were formed. In either case, the final product could not be used to prepare electrophoresis gels.

Example 2
Preparation of HEAA by Prior Art Method

HEAA was prepared according to the procedure reported by Saito et al. (*Macromolecules* 29:313–319 (1996)). It was found that the crude product from the ethyl acetate phase (before silica chromatography) contained several components and the yield of HEAA was below 20%, as indicated by HPLC analysis. The yield will be even lower after silica gel chromatography purification. The crude product could not be polymerized by APS/TEMED.

Example 3
Preparation of HPAA or HEAA by Prior Art Method

In this example, HPAA was prepared according to the procedure of Righetti (WO 97/16462).

To a 500 mL, four-neck round bottom flask equipped with a mechanical stirrer, a thermometer, a 200 mL dropping funnel, and a nitrogen inlet/outlet, 18.8 g of acryloyl chloride (0.2 moles) was added. After cooling the acryloyl chloride to -40° C. in an acetone/dry ice bath, 150 mL of anhydrous ethanol pre-cooled to -40° C. was added. To this cold solution, 30.0 g of 3-amino-1-propanol (0.4 moles) in 150 mL of anhydrous ethanol was added through the dropping funnel. The addition rate was controlled so that the reaction temperature was kept at -40° C. After the addition, the reaction was continued at 5° C. for 5 hours. Ethanol was removed by evaporation, and the residue was dissolved in acetone. After filtering out the 3-amino-1-propanol HCl salts, the acetone solution was passed through a silica column, eluted with acetone. The eluate was collected and acetone was removed by evaporation. Water was added to the residue to yield an aqueous solution of 80 g. The aqueous solution contained 14% of HPAA, according to vacuum oven analysis. This monomer solution was used for gel electrophoresis in Example 10.

HEAA was also prepared in accordance with this procedure. The method required the complete removal of ethanol by vacuum distillation. It was found that the evaporation residual is very viscous, as is the aqueous solution of the residue. Furthermore, a white precipitate was formed when the aqueous solution was mixed with acetone. This precipitation indicates that premature polymerization occurred during the evaporation step.

Example 4
Preparation of HEAA

Acetone was used as the solvent, triethylamine was used as the base to absorb the HCl generated, and water was added to the monomer before the removal of acetone to prevent polymerization of monomer.

To a one liter, four-neck round bottom flask equipped with a mechanical stirrer, a thermometer, a 400 mL dropping funnel, and a nitrogen inlet/outlet, 61 g of ethanolamine (1 mole), 101 g of triethylamine (1 mole), and 250 mL of acetone were added. The mixture was cooled down to -20° C. with an acetone/dry ice bath. To this cold solution, 94.3 g of acryloyl chloride (1 mole) in 250 mL of acetone was added through the dropping funnel. The addition rate was controlled so that the reaction temperature was kept about -20° C. After the reaction, the ethanolamine.HCl salts were filtered out. The filtrate was mixed with 300 mg of 4-methoxyphenol and 500 mL of deionized water. Acetone was removed by vacuum distillation. The remaining aqueous solution was passed through a mixed-bed ion-exchange column packed with 100 g of Amberlite™ MB-150. A total of 600 g of eluate was collected. The aqueous solution had a viscosity of only 2.0 cPs at 25° C., indicating that polymerization did not occur. However, HPLC analysis indicated that the obtained monomer was not pure. The HPLC chromatogram of reaction product is shown in FIG. 1 (top graph line). In addition to the major HEAA peak at 3.2 minutes, there was a minor peak at 11.2 minutes, which is attributed to the hybrid crosslinker, acrylamido-ethyl-acrylate.

Example 5
Preparation of HEAA

Acetonitrile was used as the solvent, ethanolamine was used as the base to absorb the HCl generated, and water was added to the monomer before the removal of acetonitrile to prevent polymerization of monomer.

To a one liter, four-neck round bottom flask equipped with a mechanical stirrer, a thermometer, a 400 mL dropping funnel, and a nitrogen inlet/outlet, 122 g of ethanolamine (2 moles), and 250 mL of acetonitrile were added. The mixture was cooled down to 0° C. with an ice/water bath. To this solution, 94.3 g of acryloyl chloride (1 mole) in 250 mL of acetonitrile was added through the dropping funnel. The addition rate was controlled so that the reaction temperature was kept about 5° C. At the end of addition, the pH of the reaction mixture was adjusted to 7 with either acryloyl chloride or ethanolamine. While keeping the reaction solution cold (below 5° C.), the ethanolamine.HCl salts were filtered out. The filtrate was mixed with 500 mL of deionized water before removing acetonitrile from the solution by vacuum distillation. The remaining aqueous solution was passed through a mixed-bed ion-exchange column packed with 100 g of Amberlite™ MB-150. A total of 600 g of eluate was collected. The solution had a viscosity of 1.8 cPs at 25° C., indicating that polymerization did not occur. HPLC analysis indicated that the product was free of any impurities. The HPLC chromatogram of the reaction product is shown in FIG. 1 (bottom graph line). There was only one peak at 3.2 minutes, and no peak was observed at 11.2 minutes. The eluate was concentrated to 400 grams, and further analyzed. Solids Content, 23% (wt/wt); pH=7.2 at 250° C.; Conductivity=14 µS/cm at 25° C.; Viscosity=2.0 cPs at 25° C. The yield of HEAA was about 80%. This monomer solution was used for gel electrophoresis in Examples 10–13.

Example 6
Preparation of HEAA

In comparison with Example 5, the deionization of this example is performed before the evaporation of acetonitrile and in a batch process instead of a column process.

To a one liter, four-neck round bottom flask equipped with a mechanical stirrer, a thermometer, a 400 mL dropping funnel, and a nitrogen inlet/outlet, 122 g of ethanolamine (2 moles), 200 mg of 4-methoxyphenol and 250 mL of acetonitrile were added. A slow nitrogen surge was used to minimize material loss during the reaction. The mixture was cooled below 0° C. with an ice/water salt bath. To this solution, 90.5 g of freshly distilled acryloyl chloride (1 mole) in 250 mL of acetonitrile was added through the dropping funnel. The addition rate was controlled so that the reaction temperature was kept below 50° C. The ethanolamine HCl salts precipitated during the reaction. At the end of addition, the pH of the reaction mixture was adjusted to 7 with either acryloyl chloride or ethanolamine. While keeping the reaction solution cold (below 5° C.), the ethanolamine HCl salts were filtered out. To the filtrate, 500 mL of deionized water and 100 g of Amberlite™ MB-150 were added. The resin was removed by filtration after agitating for one hour. The acetonitrile and part of the water were removed by vacuum rotary evaporation, maintaining solution temperature below 30° C. The miscibility of the solution was checked with acetone (1 ml of solution with 4 ml acetone), and the conductivity of the solution was measured when the residue weight reached 500 g. If the acetone mixture was clear and the conductivity was less than 10 $\mu$S/cm, the filtrate was concentrated to about 400 g by vacuum distillation. The filtrate can be concentrated to 300 g if desired. The final solution has the following properties: HEAA concentration: 23% (wt/wt); pH=7.2 at 25° C.; Conductivity=3.5 $\mu$S/cm at 25° C.; Viscosity=2.4 cPs at 25° C. The yield of HEAA was about 80%.

DOWEX MR-3C resin can be used in place of the Amberlite™ MB-150. The resin mixture is agitated until the conductivity of the supernatant is less than 2 $\mu$S/cm. Additional ion-exchange resin is added if needed.

Example 7

Preparation of HEAA

In comparison with Example 5, the reaction of this example is conducted at 1 M concentration and lower temperature, and the deionization of this example is performed before removal of acetonitrile.

To a one liter, four-neck round bottom flask equipped with a mechanical stirrer, a thermometer, a 600 mL dropping funnel, and a nitrogen inlet/outlet, 122 g of ethanolamine (2 moles), 400 mg of 4-methoxyphenol and 500 mL of acetonitrile were added. The mixture was cooled below -20° C. with a dry ice/acetone bath. To this solution, 90.5 g of freshly distilled acryloyl chloride (1 mole) in 500 mL of acetonitrile was added through the dropping funnel. The addition rate was controlled so that the reaction temperature was kept below -10° C. At the end of addition, the pH of the reaction mixture was adjusted to 7 with either acryloyl chloride or ethanolamine. While keeping the reaction solution cold (below -10° C.), the ethanolamine HCl salts were filtered out. To the filtrate, 500 mL of deionized water was added. The mixture was passed through an ion-exchange column packed with 100 g of Amberlite™ MB-150. The eluate was concentrated to about 400 g by vacuum distillation. The final solution has the following properties: HEAA concentration: 21% (wt/wt); pH=7.8 at 25° C.; Conductivity=5.6 $\mu$S/cm at 25° C.; Viscosity=2.8 cPs at 25° C. The yield of HEAA was about 73%.

Example 8

Preparation of HEAA

In comparison with Example 6, the reaction is conducted at higher concentration and lower temperature.

To a one liter, four-neck round bottom flask equipped with a mechanical stirrer, a thermometer, a 600 mL dropping funnel, and a nitrogen inlet/outlet, 122 g of ethanolamine (2 moles), 20 mg of 4-methoxyphenol and 125 ml of acetonitrile were added. The mixture was cooled below -10° C. with dry ice/acetone bath. To the agitated solution, 90.5 g of freshly distilled acryloyl chloride (1 mole) in 125 ml of acetonitrile was added through the dropping funnel. The addition rate was controlled so that the reaction temperature was kept below 0° C., while the bath temperature was maintained at -15° C. The addition took about two hours. The final reaction mixture had a pH of about 8. After removing the ethanolamine.HCl salts by filtration, the filtrate was mixed with 125 ml of DI water. The aqueous mixture was agitated with 125 g of Dowex MR-3C resin for one hour, and the supernatant conductivity was reduced from 5.0 mS/cm to 1.2 $\mu$S/cm. After removing the ion-exchange resin, the aqueous solution was concentrated by rotary evaporation to remove acetonitrile. The evaporation residue was filtered through a 0.45 micron cellulose membrane, and 230 g of clear, colorless solution was obtained. The solution has the following properties: HEAA concentration by evaporation: 40% wt.; pH 6.2; Conductivity=5.2 $\mu$S/cm; Yield: 80%.

Example 9

Preparation of N-(2-hydroxyethyl)methacrylamide (HEMAA)

To a 500 mL, four-neck round bottom flask equipped with a mechanical stirrer, a thermometer, a 200 mL dropping funnel, and a nitrogen inlet/outlet, 48.8 g of ethanolamine (0.8 moles), 80 mg of 4-methoxyphenol and 100 mL of acetonitrile were added. The mixture was cooled below 0° C. with an ice/water salt bath. To this solution, 41.8 g of freshly distilled methacryloyl chloride (0.4 mole) in 100 mL of acetonitrile was added through the dropping funnel. The addition rate was controlled so that the reaction temperature was kept below 0° C. At the end of addition, the pH of the reaction mixture was adjusted to 7 with either methacryloyl chloride or ethanolamine solution. While keeping the reaction solution cold (below 5° C.), the ethanolamine HCl salts were filtered out. To the filtrate, 200 mL of deionized water and 40 g of Dowex MR-3C resin, which was pre-washed with two bed volumes of 1/1 ratio acetonitrile/water mixture for three times, were added. The resin was removed by filtration after agitating for one hour. The filtrate was concentrated to about 160 g by vacuum distillation. The final solution has the following properties: HPLC and FT-IR analysis indicates there is no ester formation; HEMAA concentration: 23.5% (wt/wt); pH=6.9 at 250° C.; Conductivity=3.9 $\mu$S/cm at 25° C.; Viscosity=1.9 cPs at 25° C. The yield of HEMAA was about 73%.

Example 10

Preparation of N-(3-hydroxypropyl)acrylamide (HPAA)

To a 250 mL, four-neck round bottom flask equipped with a mechanical stirrer, a thermometer, a 100 mL dropping fuel, and a nitrogen inlet/outlet, 30.0 g of 1-amino-3-propanol (0.4 mole), and 100 mL of acetonitrile were added. The mixture was cooled below 0° C. with an ice/water bath. To this solution, 18.1 g of freshly distilled acryloyl chloride (0.2 mole) in 50 mL of acetonitrile was added through the dropping funnel. The addition rate was controlled so that the reaction temperature was kept below 0° C. After the addition was finished and the agitation was turned off, the reaction solution separated into two liquid phases. The bottom layer viscous salt solution phase was discarded. 100 mL of deionized water was added to the top layer acetonitrile solution phase. After removing all acetonitrile by vacuum distillation, the aqueous solution was passed through a mixed bed ion-exchange column packed with 20 g of Dowex MR-3C resin. A total of 76 grams of eluate was collected. The final solution has the following properties: HPLC and FT-IR analysis indicates there is no ester formation; HPAA concentration: 7.2% (wt/wt); pH=5.6 at 25° C.; Conductivity= 56.6 µS/cm at 25° C.; Viscosity=1.1 cPs at 25° C. The relative low yield of HPAA is due to the fact that HPAA is soluble in the salt phase. HPAA in the salt phase can be recovered by acetone extraction since HPAA is soluble in acetone, and the salt is insoluble.

N-(2-hydroxypropyl)acrylamide, N-(2-hydroxypropyl)methacrylamide, N,N-di-(2-hydroxy-ethyl)acrylamide, N-(hydroxyethyl)-N-(3-hydroxypropyl)methacrylamide, N-(1-chloro-ethyl-2-hydroxyethyl)acrylamide and N-(hydroxyethoxyethyl)acrylamide are prepared in a manner similar to that of Examples 5–9 above, using the appropriate starting materials.

Example 11

Gels for Protein Analysis

The performance of HEAA-based gels was assessed by electrophoretic separation of a 5 kD to 225 kD range molecular weight standard, and protein extracts of bacteria *E. coli*. Visualization of the results was performed by staining the gels with Coomassie Brilliant Blue. The results of HEAA-based gels were compared with those of polyacrylamide gels, DMA-based gels and BPAA-based gels. All SDS-gel electrophoresis experiments were conducted under standard discontinuous buffer condition as described by Laemmli (*Nature* 277:680–685 (1970)), except that the buffer in the stacking gel was the same as that in the resolving gel (0.375M Tris-HCl, pH=8.8). The running buffer was Tris-Glycine (250 mM Tris., 250 mM Glycine, 0.1% SDS, pH=8.3). All four vinyl monomers were mixed with a crosslinker, BIS, to form gels. The crosslinker level (%C, obtained by dividing the amount of crosslinker by the sum of the crosslinker and monomer (and optional comonomer) multiplied by 100) was kept the same in the stacking (4%T; obtained by dividing the amount of the monomer, optional comonomer and crosslinker by the total volume of the solution multiplied by 100) and resolving (10%T) gels. APS/TEMED (0.1% in final gel solution) was used to initiate polymerization. All gels were cast in Novex plastic Mini-Cassettes (10 cm×10 cm×0.1 cm). The gels were allowed to polymerize at ambient temperature for one hour before use. The gels were run in a Novex Xcell II Mini-Cell at a constant voltage of 120 V until the tracking dye reached the bottom of the gel. The gel formulations and results are summarized in Table 1.

TABLE 1

| | Protein Gel Formulations and Separation Results | | | | | | | |
|---|---|---|---|---|---|---|---|---|
| Gel Formulation | Prior Art Gel #1 | Prior Art Gel #2 | Prior Art Gel #3 | Invention Gel #4 | Invention Gel D | Invention Gel E | Invention Gel F | Invention Gel G |
| Monomer | AA | HPAA (Ex. 3) | DMA (Ex. 5) | HEAA (Ex. 5) | HEAA (Ex. 5) | HEAA (Ex. 5) | HEAA (Ex. 5) | HEAA (Ex. 5) |
| Comonomer | | | | | AA | AA | AA | AA |
| Mon.:Comon. Ratio | | | | | 25:75 | 50:50 | 75:25 | 85:15 |
| Crosslinker (c) | BIS | BIS | BIS | BIS | BIS | BIS | BIS | BIS |
| % C (weight ratio of monomer to crosslinker) | 3.3 (29:1) | 1.8 (54:1) | 2.3 (42:1) | 2.5 (39:1) | 2.5 | 2.5 | 2.5 | 2.5 |
| Resolution | Good | Poor | Very poor | Good | Good | Good | Good | Good |
| Shelf Life (4° C.) | 3 Mo. | ND | ND | 12 Mo. | 3 MO. | 3 Mo. | >6 Mo. | >6 Mo. |

ND = Not Determined

The separation range was 25–225 kD. The quality of resolution of proteins in these gels were, in descending order: HEAA-based gels=polyacrylamide gels>BPAA-based gels>DMA-based gels. DMA-based gels have the worst resolution because DMA is the most hydrophobic. The poor resolution of HPAA-based gels in comparison with polyacrylamide gels is contrary to what, was claimed by Righetti (WO 97/16462). The resolution of HEAA-based gels is comparable to that of polyacrylamide gels, indicating the hydrophilicity of HEAA is similar to that of acrylamide.

Figure 2A:
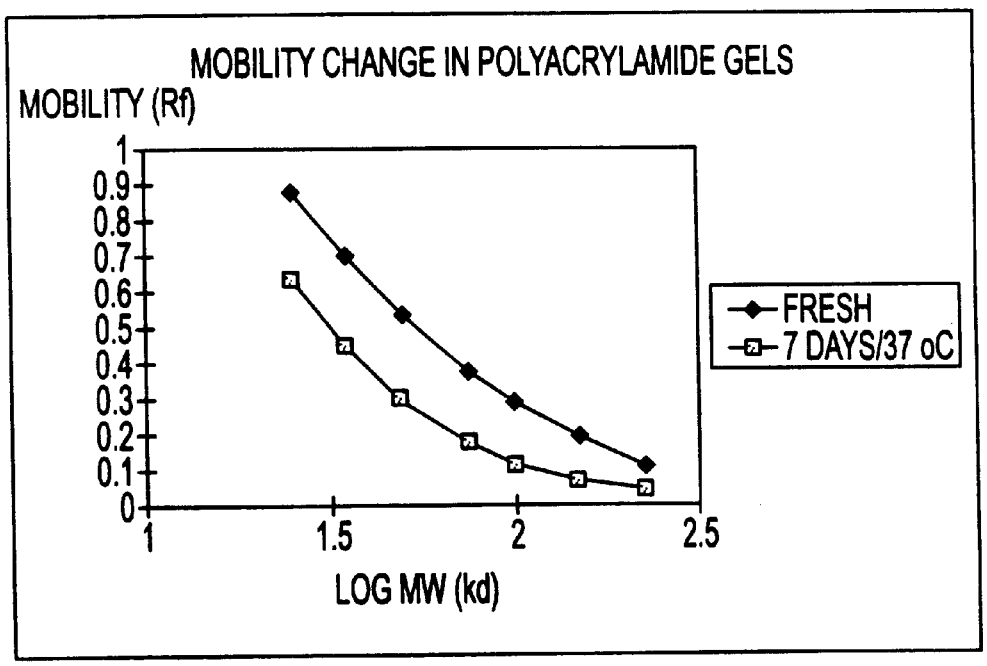
FIG. 2A uses a polyacrylamide gel and FIG. 2B uses HEAA-based gels. Mobility (Rf) was defined as the ratio of the distance migrated by protein molecule to the distance migrated by the tracking dye molecule.
Figure 2B:
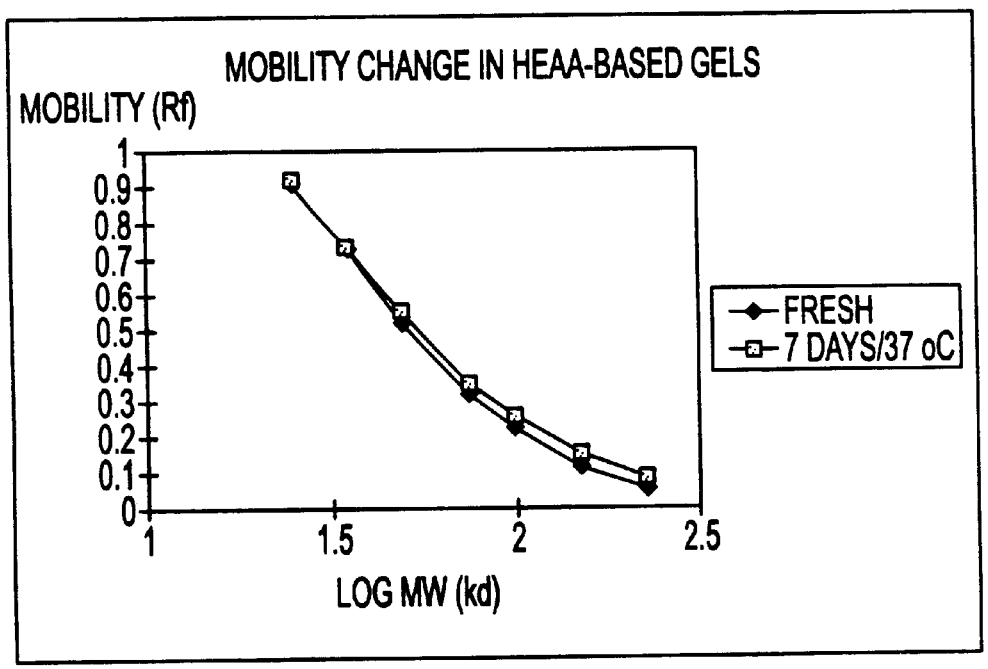
FIG. 2 shows the effect of gel aging on protein mobility during gel electrophoresis.

A large number of gels #1 and #4 were prepared and stored at 37° C. for different periods of time. The resolution of proteins irk aged gels was compared with that in fresh gels. It was found that in both cases, gel resolution deteriorated with aging, but polyacrylamide gels deteriorated at a much higher rate than HEAA-based gels. For example, polyacrylamide gels were completely useless for *E. coli* protein separation after 7 days at 37° C., but HEAA-based gels still gave reasonable resolution after 20 days at 37° C. Based on the fact that standard polyacrylamide gels have a shelf life of 3 months at 4° C., it can be extrapolated that HEAA-based gels have a shelf life of at least 12 months at 4° C. The effect of aging on protein mobility in electrophoresis gels is shown in FIG. 2. For polyacrylamide gels (FIG. 2A), there is a substantial drop of protein molecule mobility after the gels are stored at 37° C. for 7 days. This drop is attributed to the hydrolysis of acrylamide moieties. The hydrolysis results in the incorporation of negatively charged carboxyl (—COO⁻) groups onto the gel matrix, which in turn slows down the mobility of protein molecules by electroendosmosis. For HEAA-based gels (FIG. 2B), there is essentially no change in protein mobility after the gels are stored at 37° C. for 7 days, indicating that HEAA-based gels are more resistant to alkaline hydrolysis than polyacrylamide gels. For a discussion of gels D-G, see Example 15.

Example 12
Non-denaturing Gels for Double-Stranded DNA Fragments Separation The performance of HEAA-based gels was assessed by electrophoretic separation of double-stranded (ds) DNA ladders (FMC Corporation, 20 bp, 100 bp and 500 bp). Visualization of the separation results was performed by staining the gels with ethidium bromide. The results were compared with standard polyacrylamide gels. 1×TBE buffer (89 mM Tris, 89 mM boric acid, 2 mM EDTA, pH=8.3) was used as both gel buffer and running buffer. For both types of gels, BIS was used as a crosslinker, and APS/TEMED (0.1% in final gel solution) was used to initiate polymerization. All gels were cast in Novex plastic Mini-Cassettes (10 cm×10 cm×0.1 cm). The gels were set at ambient temperature for one hour before use. The gels were run in a Novex Xcell II Mini-Cell at a constant voltage of 120 V until the tracking dye reached the gel bottom. The gel formulations for ds DNA fragments separation and results are summarized in Table 2.

TABLE 2

Non-denaturing DNA Gel Formulations and Separation Results

| Gel Formulation | Prior art gel #5 | Invention gel #6 |
| --- | --- | --- |
| Monomer | AA | HEAA (Ex. 5) |
| Crosslinker | BIS | BIS |
| % C (weight ratio of monomer to crosslinker) | 3.3 (29:1) | 2.0 (49:1) |
| % T | 10 | 10 |
| Sep. Range | 40–2000 bp | 40 bp–2000 bp |
| Resolution | Good | Good |

At the same crosslinking density level, i.e., the same monomer-to-crosslinker molar ratio, HEAA-based gels have comparable separation range and resolution as polyacrylamide gels. On the basis of the data of Example 11, it is expected that HEAA-based nondenaturing gels will have longer shelf life than nondenaturing polyacrylamide gels.

Example 13
Denaturing Gels for DNA Sequencing

Denaturing polyacrylamide gels are widely used for manual and automated DNA sequencing. DNA sequencing gels require very high resolution because single-stranded DNA fragments with only one nucleotide(nt) difference among several hundreds of nucleotides need to be separated. Denaturing HEAA-based gels for DNA sequencing are assessed on a commercially available automated DNA sequencer, OpenGene™ system, Visible Genetics Inc. Gels are prepared in 50 μm-thick MicroCel™ glass cassettes from VGI by photoinitiation using a conventional photoinitiator, such as 2,2-dimethoxy-2-phenyl-acetophenone and a UV source ranging from 200 to 500 nm. Denaturants, such as urea and N-methyl-pyrrolidinone (NMP), are added into the gels to prevent the formation of any secondary structure in single-stranded DNA fragments during electrophoresis. 1×TBE buffer (Tris 89 mM, boric acid 89 mM, EDTA 2 mM, pH 8.3) is used as gel buffer as well as running buffer. M13mp18 DNA is used as template for PCR and sequencing reactions. The DNA sequence of M13mp18 is available (GeneBank Accession #X02513). Nucleotides number 23 through 523 are used to assess the quality of DNA sequence data. The numbering of nts starts at the first A (adenine) in the HindIII restriction recognition site, and increases counter-clockwise towards the AvaII restriction site of this DNA. Read length at 99% accuracy is scored. This is defined as the length of consecutive nts that are read with ≦1% error.

The primer for DNA sequencing is labeled with fluorescent dye CY5.5. The gels are run for 45 minutes at 1500 Volts and 51° C. Again, HEAA-based denaturing gels are compared with polyacrylamide denaturing gels, in terms of read length at 99% accuracy, and potential stability. The gel formulations are summarized in Table 3.

TABLE 3

DNA Sequencing Gel Formulations

| Gel Formulation | Prior art Gel #7 | Prior art Gel #8 | Invention Gel #9 | Invention Gel #10 |
| --- | --- | --- | --- | --- |
| Monomer | AA | AA | HEAA (Ex. 5) | HEAA (Ex. 5) |
| Crosslinker | BIS | BIS | BIS | BIS |
| % C (weight ratio of monomer to crosslinker) | 3.3 (29:1) | 3.3 (29:1) | 1.5 (66:1) | 1.5 (66:1) |
| % T | 6 | 7 | 6 | 7 |
| Denaturant | 7 M urea | 25% NMP | 7 M urea | 25% NMP |

It is expected that Prior art Gel #7 has a read length of 300–350 nts with 99% accuracy, because it is widely used for DNA sequencing. Since neither acrylamide nor urea is stable in TBE buffer, the shelf life of a premix solution or a precast gel made from this combination is expected to be short. In Prior art Gel #8, a stable organic denaturant, N-methyl-pyrrolidinone (NMP), is used in combination with acrylamide. It is expected that the resolution is poor and the read length is below 100 nt at 99% accuracy. This result suggests that NMP interfered with the formation of the polyacrylamide gel. It is found that both invention Gels #9 and #10 have a read length of 300–350 nts with 99% accuracy, comparable with Prior art Gel #7. Since urea is used as the denaturant in Gel #9, a premix solution or a precast gel made from this combination is not expected to have a long shelf life. However, both HEAA monomer and the NMP denaturant are stable in Gel #10, so the premix solution and precast gel are expected to have longer shelf life than Prior art Gel #7.

Example 14
Denaturing Gels for DNA Sequencing

Denaturing HEAA-based gels for DNA sequencing were tested on a commercial automated DNA sequencer, Prism™ 377 DNA sequencer (PE-Applied BioSystems, Foster City, Calif.). Gels were prepared in 0.2 mm-thick 36 cm-long glass cassettes using APS/TEMED as the polymerization initiator system, and in the absence or presence of comonomer, acrylamide. Urea was added to 36 wt % (6M) and 1×TBE was used as gel buffer as well as running buffer. M13mp18 DNA (GeneBank Accession #X02513) nucleotides 4 through 800 were used to assess the quality of resolution (nts were numbered according to Example 12). The sequencing primer was labeled with PE-Applied Biosystems' Big Dye chemistry. The gels were run for 3.5 hours at the "4×" running condition (2400 scans/hr). Read length at 98.5% was scored, defined as the length of consecutive nts that were read with ≦1.5% error.

TABLE 4

DNA Sequencing Gel Formulations

| Gel Formulation | #11 (Prior Art) | #12 (Invention) | #13 (Invention) |
| --- | --- | --- | --- |
| Monomer | Acrylamide | HEAA | Acrylamide/HEAA = 80/20 |

TABLE 4-continued

DNA Sequencing Gel Formulations

| Gel Formulation | #11 (Prior Art) | #12 (Invention) | #13 (Invention) |
|---|---|---|---|
| Crosslinker | BIS | BIS | Weight ratio BIS |
| % T | 4.5% | 6% | 5.5% |
| % C | 3.3% | 1.25% | 1.25% |
| Buffer | 1 X TBE | 1 X TBE | 1 X TBE |
| Denaturant | 6 M urea | 6 M urea | 6 M urea |
| APS | 0.05% | 0.05% | 0.05% |
| TEMED | 0.07% | 0.07% | 0.07% |
| Read length at 98.5% accuracy | 510–665 nt | 550–730 nt | 600–650 nt |

The results indicate that HEAA based gels are at least as good as acrylamide gels for automated DNA sequencing. The pre-formulated gel solution of HEAA should be more stable than a gel solution of acrylamide.

Example 15
HEAA and Acrylamide Copolymer Gels for Protein Analysis

Gels for protein analysis were prepared in accordance with Example 11 using the monomers shown in Table 5. BIS was used as crosslinker, keeping the crosslinking level (%C) constant at 2.5, and the total weight of the monomer and crosslinker at 10%T. The ratios of the different monomers (HEAA and acrylamide) were as shown in Table 5. Protein samples were analyzed on mini-gels using the method described in Example 11. The gel formulation and separation results are shown in Table 5.

TABLE 5

Protein Gel Formulations and Separation Results

| | HEAA (monomer %) | Acrylamide (monomer %) | Resolution (time zero) | Resolution (7 days at 37° C.) |
|---|---|---|---|---|
| Gel A (prior art) | | 100% | Good | Bad |
| Gel C (invention) (= #4) | 100% | | Good | Good |
| Gel D (invention) | 25% | 75% | Good | Bad |
| Gel E (invention) | 50% | 50% | Good | Bad |
| Gel F (invention) | 75% | 25% | Good | Good |
| Gel G (invention) | 85% | 15% | Good | Good |

It has been found that gels which contain 1–100% HEAA and 0–99% comonomer, such as acrylamide and others disclosed herein, all have good resolution when freshly made. It has further been found that the percentage of HEAA in the total copolymer affects the storage stability of the precast gel when the comonomer is less stable than HEAA.

Example 16
Preparation of Linear HEAA Polymers by Solution Phase Polymerization

Figure 3:
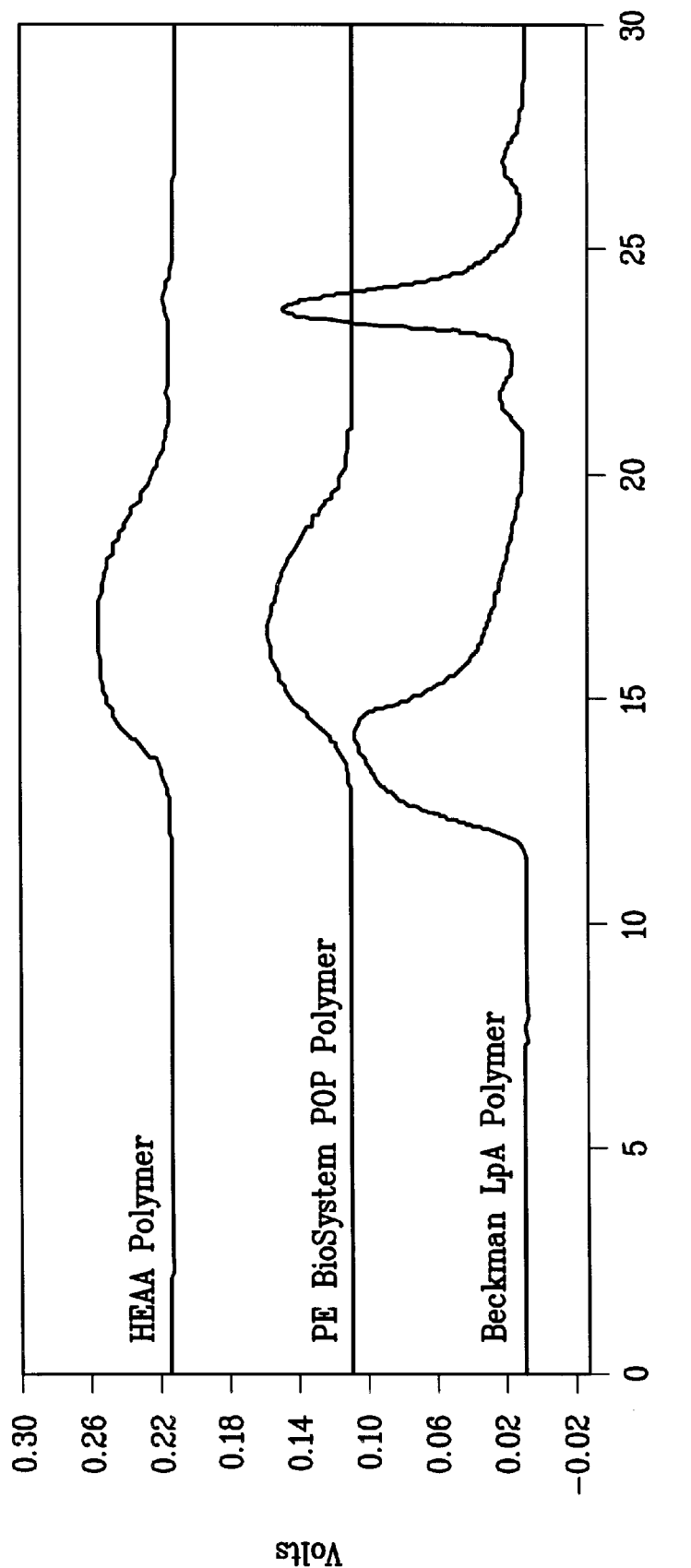
FIG. 3 shows the GPC chromatograms of HEAA homopolymer prepared by solution polymerization (Top graph), PE Biosystems' POP Polymer (Middle Graph) and Beckman's Linear Polyacrylamide (Bottom graph). GPC Column: Shodex KB-806, 10 million molecular weight exclusion limit; Mobile phase: 0.1 M sodium sulfate; Flow rate: 0.5 ml/min; Detector: 210 nm UV.

To a 50 mL round-bottom flask, 12.1 mL of 33% (w/v) HEAA solution (4 g of HEAA prepared in Example 5), 0.8 ml of isopropanol, and 7.1 mL of deionized water were added. The solution was mixed and degassed for 20 mins under 40 mm Hg vacuum. After warming the solution to 40C., 100µl of 10% APS solution and 20 µl of TEMED were added and mixed by shaking. The polymerization was conducted at 40C. for 1 hour and the resulting polymer solution was lyophilized overnight. The white solids were extracted with acetone in a Soxhlet apparatus for two hours, and then dried in a vacuum oven for two hours. A total of 3.9 grams of polymer was obtained (97.5% yield). The polymer was soluble in water at ambient temperature, and a 10% aqueous solution had a viscosity of 1030 cPs, when measured with a Brookfield viscometer (#4 spindle, 60 rpm) at 25C. The GPC chromatogram of HEAA polymer is shown in FIG. 3, in comparison with the two commercially available polymers: PE Biosystems' POP polymer and Beckman's LPA polymer. It can be seen that the HEAA polymer prepared by solution polymerization has similar molecular weight as PE Biosystems' POP polymer. According to GPC calibration by linear polyethyleneoxide standards, the average molecular weight is about 1 million Dalton. The molecular weight of Beckman's LPA is much higher, as shown by short retention time. The asymmetry GPC peak for LPA suggests that the molecular weight of LPA is close or above the molecular weight exclusion limit of the column, which is about 10 million Daltons.

Example 17
Preparation of Linear HEAA Polymers by Emulsion Polymerization

Similar to acrylamide, HEAA can be polymerized by emulsion polymerization. The procendure by Goetzinger et al. (*Electrophoresis* 19:242–248 (1998)) and Baade (*Eur. Polym J* 20:505–512 (1984)) for acrylamide was adapted for polymerization of HEAA with minor modifications.

To a 1 liter, four-neck, round bottom flask equipped with mechanical stirrer, thermometer and nitrogen inlet/outlet, 1.2 g of sorbitan monooleate, 48.8 g of petroleum special and 50 g of 40% HEAA aqueous solution are charged. A white dispersion is formed by agitating at 650 rpm. The dispersion is degassed with nitrogen purging continuously. After heating the dispersion up to 35° C. with a water bath, 5 µL of TEMED and 50 µL of 10% APS are added. Polymerization is continued for 20 hours at 35° C. After precipitating the polymer in acetone, the solid is washed with acetone several times, and vacuum dried to obtain 18 g of white powder. Yield is 90%. GPC data indicates that the polymer has an average molecular weight of 6 million Daltons.

Example 18
DNA Sequencing by Capillary Electrophoresis

The HEAA polymer prepared by solution polymerization was tested for sequencing DNA by capillary electrophoresis using a home-made instrument as described by Yeung (U.S. Pat. No. 5,006,210). The HEAA polymer matrix was prepared by dissolving the solids in 1×TBE and 7M urea buffer to make up a 6% polymer solution. Electrophoresis was conducted at ambient temperature (25° C.) with moderately high field (150 V/cm). Bare capillaries with 75 µm internal diameter, 60 cm total length and 50 cm effective length was used. The sequencing products were obtained using a pGEM template and PE Biosystems' dRhodamine dye terminators with either one color (T) or four colors labeled (U.S. Pat. No. 5,741,411). The read length was assessed based on the chromatographic resolution of the individual sequencing fragments, rather than a software-based base output. This approach has been used previously (Li and Yeung, *Applied Spectroscopy* 49:1528–1533 (1995)). The HEAA polymers were compared with the two commercially available matrices based on polyacrylamide (Beckman) and poly(N,N-dimethylacrylamide) (POP, PE BioSystems) in terms of read length, viscosity and run speed. The two commercially available polymer matrices were used as received. The comparative results are summarized in Table 6.

TABLE 6

| Media | Beckman "LPA" | PE Biosystems "POP" | Invention media I | Invention media II |
|---|---|---|---|---|
| Base polymer | Poly-acrylamide | Poly (N,N-dimethyl-acrylamide) | HEAA polymer | HEAA polymer |
| Apparent MW | ~10 × $10^6$ | ~1 × $10^6$ | ~6 × $10^6$ | ~1 × $10^6$ |
| Read Length (nts) | 700 | 300 | 600 | 400 |
| Run Speed (nts/min.) | 2.55 | 1.82 | 2.8 | 2.76 |

Consistent with the molecular weight estimates, Beckman's linear polyacrylamide (LPA) had the highest viscosity, while the viscosities of the HEAA polymer in Invention media II, and PE Biosystems' POP polymer were comparable.

The read length results confirm the finding by Karger and Yeung that use of a high molecular weight polymer is beneficial for resolving large DNA fragments (*Electrophoresis* 19:242–248 (1998); *J Chromatogr A* 781:315–25 (1997)). These results showed that Beckman's LPA gave the best read length of the linear polyacrylamides tested. At comparable viscosity, the HEAA polymer matrix surprisingly out-performed PE Biosystems' POP polymer in both read length, by 100 nts, and in of run speed. The higher resolution and faster run speed of the HEAA polymer compared to the POP polymer is unexpected from the prior art. It is believed that the higher resolution and faster run speed is attributable to the higher hydrophilicity of the HEAA polymer, which minimizes the hydrophobic interaction seen between dye-labeled DNA fragments and polymer, which is especially noticeable with the POP polymer.

These results further demonstrate that all four polyacrylamide polymers can be used with bare capillaries. Generally, high molecular weight and high hydrophobicity will favor adsorption, and therefore will be more effective in suppressing EEO. However, if the molecular weight is too high the polyacrylamide polymer cannot be completely replaced between runs, and the residual polyacrylamide from previous runs will hydrolyze to cause EEO. If the hydrophobicity of the polymer is too high, the polymer has less desirable resolution. Although the HEAA polymer is more hydrophilic than the POP polymer at a comparable molecular weight, it is still effective for self-coating capillaries to suppress EEO. The unexpected combined properties of suppression of EEO by adsorption to the capillary wall, high run speed and high resolution of HEAA-based polymers are desirable for high throughput DNA analysis in capillary or microchannel-based separations.

Example 19
Short Tandem Repeat Sizing

The sizing capability of slab gel electrophoresis and of capillary electrophoresis (CE) for short tandem repeat (STR) fragments is compared using the technique described by Deforce et al. (*J. Chromatogr* 8:149–155 (1998)). Both systems used automated laser fluorescence detection to detect four fluorescent dyes, enabling the use of an internal lane standard within each sample. The STR fragments are amplified using a multiplex polymerase chain reaction in which the STR fragments Hum CD-4, Hum TH01, Hum D21S11 and Hum SE33 are amplified simultaneously. The reproducibility of the size calling is determined for both systems. The CE system produced results comparable to those obtained on the slab gel system.

INDUSTRIAL UTILITY

Hydrophilic monomers are prepared simply and on a large scale in accordance with the present invention. The hydrophilic monomers, particularly HEAA, are useful for preparing electrophoretic compositions and gels and are further useful for coating capillary tubes. The electrophoretic compositions and gels can be used for any electrophoretic method to separate macromolecules or sequence DNA or the like, including capillary electrophoresis. In addition, the hydrophilic monomers can be used in any application in which related (meth)acrylate monomers, especially hydrophilic (meth)acrylate monomers, are used. Such applications include gel beads for chromatography separation, coatings for contact lenses, monomers for preparing contact lenses, water-soluble polymeric compositions and the like.

The present invention may be embodied in other specific forms without departing from the spirit or essential attributes thereof and, accordingly, reference is made to the appended claims, rather than the foregoing specification, as indicating the scope of the invention.

What is claimed is:

1. A sieving medium for capillary and microchannel electrophoresis which comprises an aqueous solution of 0.001–30% wt/vol of a linear polymer formed from a monomer composition comprise 1–100 wt % of a hydrophilic monomer and 0–99 wt % of comonomer in an electrophoresis-comparable buffer, said hydrophilic monomer selected from the group consisting of N-(2-hydroxyethyl)acrylamide, N-(2-hydroxyethyl) methacrylamide, N,N-di(hydroxyalkyl)acrylamide, N,N-di (hydroxyalkyl) methacrylamide and mixtures thereof.

2. The sieving medium of claim 1, wherein said monomer composition comprises 10–100 wt % of said hydrophilic monomer and 0–90 wt % of a comonomer.

3. The sieving medium of claim 1, wherein said monomer composition comprises 20–100 wt % of said hydrophilic monomer and 0–80 wt % of a comonomer.

4. The sieving medium of claim 1, wherein said monomer composition comprises 30–100 wt % of said hydrophilic monomer and 0–70 wt % of a comonomer.

5. The sieving medium of claim 1, wherein said hydrophilic monomer comprises N-(2-hydroxyethyl)acrylamide.

6. The sieving medium of claim 1, wherein said monomer composition comprises about 75 wt % N-(2-hydroxyethyl) acrylamide and about 25 wt % acrylamide.

7. The sieving medium of claim 1, wherein said monomer composition comprises 100 wt % N-(2-hydroxyethyl) acrylamide.

8. A sieving medium for capillary and micro-channel electrophoresis which comprises an aqueous solution of a linear polymer comprising 1–100 wt % of a hydrophilic monomer and 0–99 wt % of a comonomer, said hydrophilic monomer selected from the group consisting of N-(2-hydroxyethyl)acrylamide, N-(2-hydroxyethyl) methacrylamide, N,N-di(hydroxyalkyl)acrylamide, N,N-di (hydroxyalkyl)-methacrylamide and mixtures thereof.

9. The sieving medium of claim 8, wherein said monomer composition comprises 10–100 wt % of said hydrophilic monomer and 0–90 wt % of a comonomer.

10. The sieving medium of claim 8, wherein said monomer composition comprises 20–100 wt % of said hydrophilic monomer and 0–80 wt % of a comonomer.

11. The sieving medium of claim 8, wherein said monomer composition comprises 30–100 wt % of said hydrophilic monomer and 0–70 wt % of a comonomer.

12. The sieving medium of claim 8, wherein said hydrophilic monomer comprises N-(2-hydroxyethyl)acrylamide.

13. The sieving medium of claim 8, wherein said monomer composition comprises about 75 wt % N-(2-hydroxyethyl)acrylamide and about 25 wt % acrylamide.

14. The sieving medium of claim 8, wherein said monomer composition comprises 100 wt % N-(2-hydroxyethyl)acrylamide.

15. A method for separating molecules in an electric field which comprises contacting a mixture of molecules with a separation medium while being subjected to an electric field sufficient to cause separation of said molecules in said separation medium, wherein said separation medium comprises either (a) a gel comprising the product formed by crosslinking polymerization of a monomer composition comprising 1–100 wt % of a hydrophilic monomer and 0–99 wt % of a comonomer, said hydrophilic monomer selected from the group consisting of N-(2-hydroxyethyl) acrylamide, N,N-di(hydroxyalkyl)acrylamide, N,N-di (hydroxyalkyl)methacrylamide and mixtures thereof, or (b) a sieving medium comprising an aqueous solution of a linear polymer formed from a monomer composition comprising 1–100wt % of a hydrophilic monomer and 0–99 wt % of a comonomer said hydrophilic monomer selected from e group consisting of N-(2-hydroxyethyl) acrylamide, N-(2-hydyethyl)methacrylamide, N,N-di(hydroxyalkyl) acrylamide, N,N-di(hydroxyalkyl)-methacrylamide and mixtures thereof.

16. The method of claim 15, wherein said monomer composition comprises 10–100 wt % of said hydrophilic monomer and 0–90 wt % of a comonomer.

17. The method of claim 15, wherein said monomer composition comprises 20–100 wt % of said hydrophilic monomer and 0–80 wt % of a comonomer.

18. The method of claim 15, wherein said monomer composition comprises 30–100 wt % of said hydrophilic monomer and 0–70 wt % of a comonomer.

19. The method of claim 15, wherein said hydrophilic monomer comprises N-(2-hydroxyethyl)acrylamide.

20. The method of claim 15, wherein said monomer composition comprises about 75 wt % N-(2-hydroxyethyl)acrylamide and about 25 wt % acrylamide.

21. The method of claim 15, wherein said monomer composition comprises 100 wt % N-(2-hydroxyethyl)acrylamide.

22. The method of claim 15, wherein the separation medium comprises said gel.

23. The method of claim 15, wherein the separation medium comprises said sieving medium.

24. The method of claim 23, wherein said sieving medium is used for capillary electrophoresis and said sieving medium suppresses electroendoosmosis.

25. The method of claim 23, wherein said monomer composition comprises 100 wt % N-(2-hydroxyethyl)acrylamide.

26. An electrophoretic gel comprising the product formed by crosslinking polymerization of a monomer composition comprising about 95–5 wt % of a hydrophilic monomer selected from the group consisting of N-(2-hydroxyethyl) acrylamide and N-(2-hydroxyethyl)methacrylamide and about 5–95 wt % of acrylamide and mixtures thereof.

27. The gel of claim 26, wherein said monomer composition comprises about 90–10 wt % of said hydrophilic monomer and about 10–90 wt % of acrylamide.

28. The gel of claim 26, wherein said monomer composition comprises about 80–20 wt % of said hydrophilic monomer and about 20–80 wt % of acrylamide.

29. The gel of claim 26, wherein said monomer composition comprises about 810–30 wt % of said hydrophilic monomer and about 30–70 wt % of acrylamide.

30. The gel of claim 26, wherein said monomer composition comprises about 95 wt % N-(2-hydroxyethyl) acrylamide and about 5 wt % acrylamide.

31. The gel of claim 26, wherein said monomer composition comprises about 75 wt % N-(2-hydroxyethyl) acrylamide and about 25 wt % acrylamide.

32. The gel of claim 26, which further comprises N,N'-methylene bisacrylamide as a crosslinker.

33. An electrophoretic gel comprising a polymer comprised of about 95–5 wt % of a hydrophilic monomer selected from the group consisting of N-(2-hydroxyethyl) acrylamide and N-(2-hydroxyethyl)methacrylamide and about 5–95 wt % of acrylamide and mixtures thereof.

34. The gel of claim 33, wherein said monomer composition comprises about 90–10 wt % of said hydrophilic monomer and about 10–90 wt % of acrylamide.

35. The gel of claim 33, wherein said monomer composition comprises about 80–20 wt % of said hydrophilic monomer and about 20–80 wt % of acrylamide.

36. The gel of claim 33, wherein said monomer composition comprises about 70–30 wt % of said hydrophilic monomer and about 30–70 wt % of acrylamide.

37. The gel of claim 33, wherein said monomer composition comprises about 95 wt % N-(2-hydroxyethyl) acrylamide and about 5 wt % acrylamide.

38. The gel of claim 33, wherein said monomer composition comprises about 75 wt % N-(2-hydroxyethyl) acrylamide and about 25 wt % acrylamide.

39. The gel of claim 33, which further comprises N,N'-methylene bisacrylamide as a crosslinker.

40. A composition for preparing an electrophoretic get which comprises 3–30%T of a monomer composition and about 0.01 to about 2.0%C of a crosslinker in an electrophoresis-compatible buffer, said monomer composition comprising about 95–5 wt % of a hydrophilic monomer selected from the group consisting of N-(2-hydroxyethyl) acrylamide and N-(2-hydroxyethyl)methacrylamide and about 5–95 wt % of acrylamide.

41. The composition of claim 40, which further comprises 2–55% wt/vol of a denaturant.

42. The composition of claim 40, wherein said monomer composition comprises about 90–10 wt % of said hydrophilic monomer and about 10–90 wt % of acrylamide.

43. The composition of claim 40, wherein said monomer composition comprises about 80–20 wt % of said hydrophilic monomer and about 20–80 wt % of acrylamide.

44. The composition of claim 40, wherein said monomer composition comprises about 70–30 wt % of said hydrophilic monomer and about 30–70 wt % of acrylamide.

45. The composition of claim 40, wherein said monomer composition comprises about 95 wt % N-(2-hydroxyethyl) acrylamide and about 5 wt % acrylamide.

46. The composition of claim 40, wherein said monomer composition comprises about 75 wt % N-(2-hydroxyethyl) acrylamide and about 25 wt % acrylamide.

47. The composition of claim 40, which further comprises N,N'-methylene bisacrylamide as a crosslinker.

48. A method for coating a tube for capillary electrophoresis which comprises contacting a capillary having an inner surface having a vinyl group attached thereto with a monomer composition comprising 1–100 wt % of a hydrophilic monomer and 0–99 wt % of a comonomer under conditions sufficient to polymerize said monomer composition to said vinyl monomer, said hydrophilic monomer selected from the group consisting of N-(2-hydroxyethyl)acrylamide and N-(2-hydroxyethyl)methacrylamide and mixtures thereof; or contacting a capillary with a polymer comprised of 1–100 wt % of a hydrophilic monomer and 0–99 wt % of a comonomer, said hydrophilic monomer selected from the group consisting of N-(2-hydroxyethyl)acrylamide and N-(2-hydroxyethyl)methacrylamide and mixtures thereof.

49. The method of claim 40, comprising contacting a capillary having an inner surface having a vinyl group attached thereto with a monomer composition comprising 1–100 wt % of a hydrophilic monomer and 0–99 wt % of a comonomer under conditions sufficient to polymerize said monomer composition to said vinyl monomer, said hydrophilic monomer selected from the group consisting of N-(2-hydroxyethyl)acrylamide and N-(2-hydroxyethyl)methacrylamide and mixtures thereof.

50. The method of claim 49, wherein said monomer composition comprises 10–100 wt % of said hydrophilic monomer and 0–90 wt % of a comonomer.

51. The method of claim 49, wherein said monomer composition comprises 20–100 wt % of said hydrophilic monomer and 0–80 wt % of a comonomer.

52. The method of claim 49, wherein said monomer composition comprises 30–100 wt % of said hydrophilic monomer and 0–70 wt % of a comonomer.

53. The method of claim 49, wherein said hydrophilic monomer comprises N-(2-hydroxyethyl)acrylamide.

54. The method of claim 49, wherein said monomer composition comprises about 75 wt % N-(2-hydroxyethyl)acrylamide and about 25 wt % acrylamide.

55. The method of claim 49, wherein said monomer composition comprises 100 wt % N-(2-hydroxyethyl)acrylamide.

56. The method of claim 48, comprising contacting a capillary with a polymer comprised of 1–100 wt % of a hydrophilic monomer and 0–99 wt % of a comonomer, said hydrophilic monomer selected from the group consisting of N-(2-hydroxyethyl)acrylamide and N-(2-hydroxyethyl)methacrylamide and mixtures thereof.

57. The method of claim 56, wherein said monomer composition comprises 10–100 wt % of said hydrophilic monomer and 0–90 wt % of a comonomer.

58. The method of claim 56, wherein said monomer composition comprises 20–100 wt % of said hydrophilic monomer and 0–80 wt % of a comonomer.

59. The method of claim 56, wherein said monomer composition comprises 30–100 wt % of said hydrophilic monomer and 0–70 wt % of a comonomer.

60. The method of claim 56, wherein said hydrophilic monomer comprises N-(2-hydroxyethyl)acrylamide.

61. The method of claim 56, wherein said monomer composition comprises about 75 wt % N-(2-hydroxyethyl)acrylamide and about 25 wt % acrylamide.

62. The method of claim 56, wherein said monomer composition comprises 100 wt % N-(2-hydroxyethyl)acrylamide.

63. The method of claim 57, wherein said monomer composition comprises 100 wt % N-(2-hydroxyethyl)acrylamide.

* * * * *